US 11,660,144 B2

(12) United States Patent
Garcia et al.

(10) Patent No.: US 11,660,144 B2
(45) Date of Patent: May 30, 2023

(54) FIDUCIAL MARKER WITH FEEDBACK FOR ROBOTIC SURGERY

(71) Applicant: Zimmer Biomet CMF and Thoracic, LLC, Jacksonville, FL (US)

(72) Inventors: Saddy Garcia, St. Augustine, FL (US); Florian Coiseur, Lattes (FR)

(73) Assignee: Zimmer Biomet CMF and Thoracic, LLC, Jacksonville, FL (US)

(*) Notice: Subject to any disclaimer, the term of this patent is extended or adjusted under 35 U.S.C. 154(b) by 707 days.

(21) Appl. No.: 16/561,699

(22) Filed: Sep. 5, 2019

(65) Prior Publication Data

US 2020/0069376 A1    Mar. 5, 2020

Related U.S. Application Data

(60) Provisional application No. 62/727,332, filed on Sep. 5, 2018.

(51) Int. Cl.
*A61B 34/30*    (2016.01)
*A61B 34/20*    (2016.01)
(Continued)

(52) U.S. Cl.
CPC .............. *A61B 34/20* (2016.02); *A61B 34/10* (2016.02); *A61B 34/30* (2016.02); *A61B 90/39* (2016.02);
(Continued)

(58) Field of Classification Search
CPC ......... A61B 34/10; A61B 34/20; A61B 34/30; A61B 34/76; A61B 90/00; A61B 90/39;
(Continued)

(56) References Cited

U.S. PATENT DOCUMENTS

| 5,551,429 A | 9/1996 | Fitzpatrick |
| 7,643,867 B2 | 1/2010 | Solar et al. |

(Continued)

FOREIGN PATENT DOCUMENTS

| CN | 112770691 A | 5/2021 |
| EP | 1647228 A2 | 4/2006 |

(Continued)

OTHER PUBLICATIONS

"European Application Serial No. 19780457.8, Response to Communication pursuant to Rules 161(1) and 162 EPC filed Nov. 1, 2021", 12 pgs.

(Continued)

*Primary Examiner* — Vi X Nguyen
(74) *Attorney, Agent, or Firm* — Schwegman, Lundberg & Woessner, P.A.

(57) ABSTRACT

A fiducial marker includes a fastener and a feedback component to provide a registration signal when engaged by a probe. The feedback component includes light-up cap, a conducting component, a magnetic component and an RFID tag. A cap for registering fiducial markers with robotic surgical systems includes a housing, a socket in the housing for coupling to a fastener, an access port in the housing, a switch disposed in the housing proximate the access port, and a sensory indicator device coupled to the switch, wherein the sensory indicator device produces a signal when activated through the access port to confirm marker contact. Methods of registering a fiducial marker fastener, such as with robotic surgical systems, include manipulating a probe to align with a signal-producing feedback component attached to or integrated with the fastener, and engaging the feedback component with the probe to activate a sensory feedback indicator.

23 Claims, 14 Drawing Sheets

(51) Int. Cl.
*A61B 34/10* (2016.01)
*A61B 90/00* (2016.01)
*A61B 34/00* (2016.01)

(52) U.S. Cl.
CPC .............. *A61B 34/76* (2016.02); *A61B 90/361* (2016.02); *A61B 90/37* (2016.02); *A61B 2034/2055* (2016.02); *A61B 2034/2068* (2016.02); *A61B 2090/363* (2016.02); *A61B 2090/364* (2016.02); *A61B 2090/3937* (2016.02); *A61B 2090/3983* (2016.02)

(58) Field of Classification Search
CPC .. A61B 19/201; A61B 19/203; A61B 19/5244
See application file for complete search history.

(56) References Cited

U.S. PATENT DOCUMENTS

| | | | |
|---|---|---|---|
| 8,457,790 | B2 | 6/2013 | Blondel et al. |
| 8,884,618 | B2 | 11/2014 | Mahfouz |
| 8,888,782 | B2 | 11/2014 | Smith et al. |
| 9,675,461 | B2 | 6/2017 | Mahfouz |
| 2004/0030237 | A1* | 2/2004 | Lee .................. A61B 34/20 600/414 |
| 2004/0167391 | A1 | 8/2004 | Solar et al. |
| 2015/0196369 | A1 | 7/2015 | Glossop |
| 2017/0231715 | A1 | 8/2017 | Roger et al. |
| 2017/0319280 | A1 | 11/2017 | Chang et al. |
| 2018/0078332 | A1 | 3/2018 | Mozes et al. |
| 2018/0193097 | A1* | 7/2018 | Mclachlin .............. A61B 34/20 |

FOREIGN PATENT DOCUMENTS

| | | |
|---|---|---|
| WO | WO-2018032084 A1 | 2/2018 |
| WO | WO-2020051316 A1 | 3/2020 |

OTHER PUBLICATIONS

"International Application Serial No. PCT/US2019/049724, International Preliminary Report on Patentability dated Mar. 18, 2021", 14 pgs.

"International Application Serial No. PCT/US2019/049724, International Search Report dated Dec. 10, 2019", 7 pgs.

"International Application Serial No. PCT/US2019/049724, Written Opinion dated Dec. 10, 2019", 12 pgs.

"Canadian Application Serial No. 3,111,325, Non Final Office Action dated May 9, 2022", 4 pgs.

"Canadian Application Serial No. 3,111,325, Response filed Sep. 7, 2022 to Non Final Office Action dated May 9, 2022", 26 pgs.

* cited by examiner

FIDUCIAL MARKER WITH FEEDBACK FOR ROBOTIC SURGERY

CLAM OF PRIORITY

This application claims the benefit of U.S. Provisional Patent Application Ser. No. 62/727,332, filed on Sep. 5, 2018, the benefit of priority of which is claimed hereby, and which is incorporated by reference herein in its entirety.

TECHNICAL FIELD

This document pertains generally, but not by way of limitation, to devices and methods for robot-assisted surgical procedures, such those involving the use of articulating arms that can be moved about multiple axes. More specifically, but not by way of limitation, the present application relates to fiducial markers that can be used to register anatomies with robotic surgical systems.

BACKGROUND

Imaging of anatomical features can be useful in preparing for and performing surgical procedures. In some procedures it can be desirable to register the shape of the anatomy in the obtained images with another frame of reference, such as the physical space of an operating room. The physical space of the operating room can be correlated to a frame of reference for a robotic surgical system. As such, it can be advantageous to ensure that the physical shape of the anatomy is recorded in imaging in such a manner that can be reproduced in the operating room.

In an example registration process, fiducial markers that can be recognized in imaging are preoperatively placed in the anatomy of a patient. The fiducial markers can comprise fasteners having a geometry that is recognizable in imaging. Multiple fiducial markers are placed on the anatomy and can be used by a physician or surgeon for planning the surgical procedure, such as by providing a reference location for where an incision or cut can be located and/or a trajectory of an instrument. After the preoperative imaging and planning, the patient with the implanted fiducial markers is brought into the physical space of the operating room. The anatomy of the patient can be immobilized and then the fiducial markers can be utilized to register the anatomy relative to the physical space of the operating room and any system associated with the referencing device. This registration can create an association between the location of the fiducial markers on the anatomy of the patient and the locations of the markers on the imaging, which can be tied back to a coordinate system for the robotic surgical system.

Examples of fiducial markers that can be used in registration procedures are described in U.S. Pat. No. 7,643,867 to Solar et al.; U.S. Pat. No. 5,551,429 to Fitzpatrick et al.; and U.S. Pub. No, 2017/0231715 to Roger et al.

OVERVIEW

The present inventors have recognized, among other things, that a problem to be solved can include the inability or reduced ability of surgeons to recognize when a fiducial marker has been satisfactorily referenced by a referencing device. For example, the fiducial marker can be difficult to recognize when a referencing device touches the fiducial marker at the exact spot where it will be recognized in imaging or by a robotic surgical system. Fiducial markers can include a divot into which a tip of the referencing device is to be positioned to perform the registration of the fiducial marker. The divot is intended to ensure the tip of the referencing device is positioned in the same location each time it is referenced or registered. The divot can enhance the accuracy of the registration process. However, within the physical constraints of the anatomy the fiducial marker can be obstructed or partially obstructed by tissue. Furthermore, the present inventors have additionally recognized that it can be difficult to recognize when a robotic assisted referencing device touches the divot. For example, in a robotic surgical system, the surgeon might be located a distance from the fiducial marker and the tip of the referencing device thereby making viewing of the divot and the tip of the referencing device difficult.

The present subject matter can provide a solution to these and other problems, such as by providing a fiducial marker that can provide feedback, such as a physical or sensory indication, of when the fiducial marker has been engaged by a referencing device in a correct location for registration. In an example, a fiducial marker can include a light-emitting indicator that can be actuated when a tip of a referencing tool engages a divot of a fiducial marker. The light-emitting indicator can be configured to not activate if the tip only touches the side of the fiducial marker. As such, the light-emitting indicator can be configured to activate when the tip touches the center of the divot or fiducial marker, thereby providing a visual indicator to a surgeon at the fiducial marker. The indicator can also be communicated to the controls of a robotic surgical system, that the referencing tool has properly engaged the fiducial marker. Such fiducial markers of the present disclosure can reduce the time of performing surgical procedures, such as by reducing the time for the registration process, and can reduce errors in registering fiducial markers thereby improving the accuracy of subsequently performed surgical procedures.

In an example, a fiducial marker can comprise a fastener comprising a threaded shaft and a head connected to the threaded shaft, and a feedback component attached to the fastener, wherein the feedback component is configured to provide a registration signal when engaged by a probe. The feedback component can comprise a housing attached to the head that can comprise an access port disposed in a first end of the housing, a switch disposed in the housing proximate the access port, and a light source electronically coupled to the switch, wherein the light source is configured to emit light when the switch is activated through the access port, or can be integral with the head of the fastener, the feedback component being selected from the group consisting of a conducting material, a magnetic material and a radio frequency identification tag.

In another example, a cap for use in registering a fiducial marker with a robotic surgical system can comprise a housing, a socket disposed in a first end of the housing configured to couple to a component for the robotic surgical system, an access port disposed in a second end of the housing opposite the socket, a switch disposed in the housing proximate the access port, and a sensory indicator device coupled to the switch, wherein the sensory indicator device is configured to produce an electronic signal when the switch is activated through the access port to provide sensory confirmation that the fiducial marker has been engaged.

In an additional example, a method of registering a fiducial marker, such as with a robotic surgical system, can comprise attaching or integrating a signal-producing cap to or with a component of the robotic surgical system, manipulating a pointer probe to align the signal-producing cap and the fiducial marker fastener with the pointer probe, engaging a probe tip of the pointer probe, a switch attached to the signal-producing cap and the fiducial marker fastener to activate a sensory feedback indicator, receiving the sensory feedback indicator from the signal-producing cap, and recording a location for the fiducial marker fastener in a coordinate system for the robotic surgical system.

This overview is intended to provide an overview of subject matter of the present patent application. It is not intended to provide an exclusive or exhaustive explanation of the invention. The detailed description is included to provide further information about the present patent application.

Figure 1:
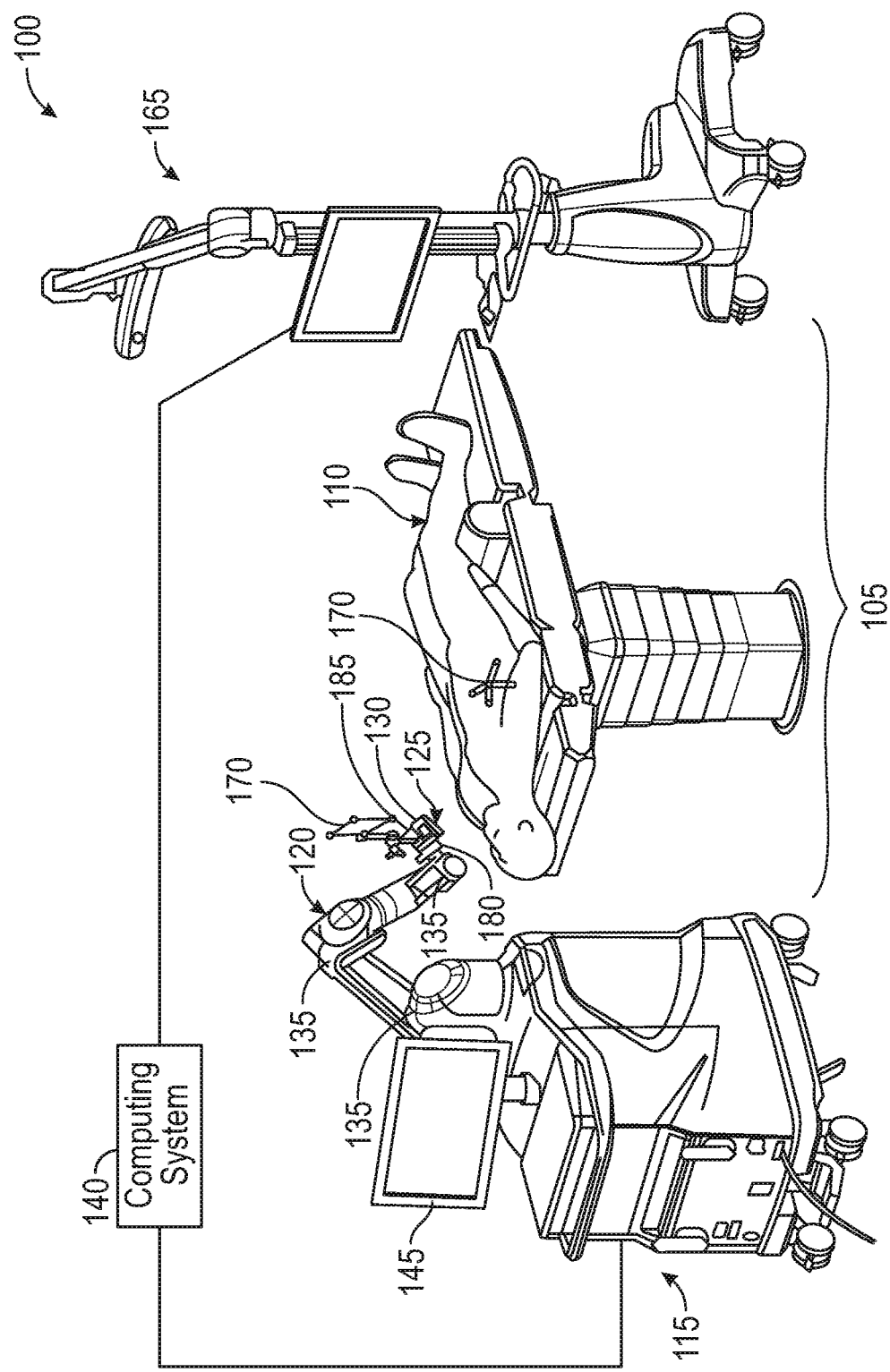
FIG. 1 is a diagrammatic view of an operating room including a robot-assisted surgical system comprising a robotic arm, a computing system and a tracking system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like, Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1; one or more passive surgical support arms can be incorporated into surgical system 100 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a gripping device such as a pincer grip, a burring device, a reaming device, an impactor device such as a humeral head impactor, a pointer, a probe or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with a probe instrument, e.g., pointer probe 200 (FIG. 2), to register surgical area 105 to computing system 140.

Robotic system 115 can also include computing system 140 that can operate robotic arm 120 and surgical instrument 125. Computing system 140 can include at least memory, a processing unit, and user input devices, as will be described herein. Computing system 140 can also include human interface device 145 for providing images for a surgeon to be used during surgery. Computing system 140 is illustrated as a separate standalone system, but in some examples computing system 140 can be integrated into robotic system 115. Human interface device 145 can provide images, including but not limited to three-dimensional images of bones, glenoid, joints, and the like. Human interface device 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Specifically, a virtual model of the anatomy of patient 110 can be created by defining anatomical points within the images) and/or by fitting a statistical anatomical model to the image data. The virtual model, along with virtual representations of implants, can be used for calculations related to the desired height, depth, inclination angle, or version angle of an implant, stem, surgical instrument, or the like related to be utilized in surgical area 105. In another procedure type, the virtual model can be utilized to determine insertion location, trajectory and depth for inserting an instrument. The virtual model can also be used to determine bone dimensions, implant dimensions, bone fragment dimensions, bone fragment arrangements, and the like. Any model generated, including three-dimensional models, can be displayed on human interface device 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Tracking system 165 can monitor a plurality of tracking elements, such as tracking elements 170, affixed to objects of interest to track locations of multiple objects within the surgical field. Tracking system 165 functions to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within a virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force and torque data or information to computing system 140 of robotic system 115. Force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

As discussed herein, in order to ensure that computing system 140 is moving robotic arm 120 in a known and fixed relationship, or in a real-time continuously updated relationship, to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure (such as for registration purposes during surgery) or post-procedure (such as for verification purposes at the end of surgery). For example, a plurality of fiducial markers can be attached to patient HO, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. As such, the real-world, three-dimensional geometry of the anatomy attached to the fiducial markers can be correlated to the anatomy in the images and movements of instruments 125 attached to robotic arm 120 based on the images will correspondingly occur in surgical area 105. Fiducial markers described herein can facilitate the registration process by providing feedback, such as visual or other sensory feedback that can be electronically generated, to a surgeon or operator of surgical system 100 to ensure that instrument 125 attached to robotic arm 120 adequately engages each fiducial marker.

Figure 2:
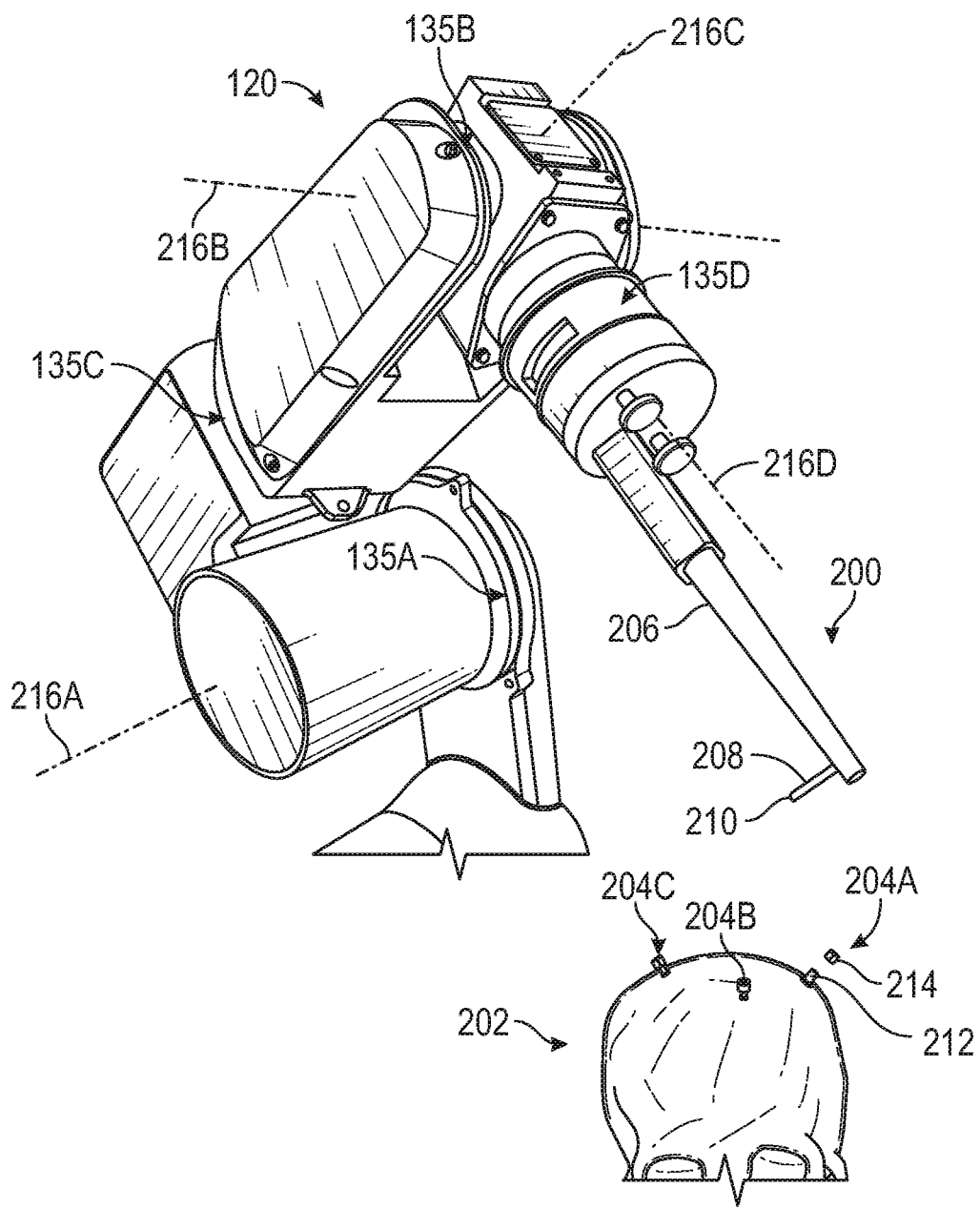
FIG. 2 is a schematic view of the robotic arm of FIG. 1 including a pointer probe shown positioned relative to a skull having fiducial markers implanted therein.

FIG. 2 is a schematic view of robotic arm 120 of FIG. 1 including pointer probe 200 shown positioned relative to skull 202 having fiducial markers 204A, 204B and 204C implanted therein. Pointer probe 200 can include shaft 206, probe extension 208 and probe tip 210. As shown with reference to fiducial marker 204A, fiducial markers 204A 204C can include fastener 112 and light-up cap 214. Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to register the anatomy and geometry of skull 202 to surgical system 100 (FIG. 1), robotic arm 120 can be manipulated automatically by computing system 140, using incremental micro-movements, for example, or a surgeon manually operating computing system 140 to engage probe tip 210 with each of fiducial markers 204A, 204B and 204C. For example, robotic arm 120 can be manipulated along axes 216A-216D to engage probe tip 210 with the center of each fiducial marker 204A 204C. Thus, it can require skill and dexterity to ensure probe tip 210 engages fiducial markers 204A-204C.

In additional examples, robotic arm 120 can be separately registered to the coordinate system of surgical system 100, such via use of a tracking element 170. Fiducial markers 204A-204C can additionally be separately registered to the coordinate system of surgical system 100 via engagement with a probe having a tracking element 170 attached thereto. As such, some or all of the components of surgical system 100 can be individually registered to the coordinate system and, if desired, movement of such components can be continuously or intermittently tracked with a tracking element 170.

It can be a difficult task to ensure that probe 200 properly seats against each of fiducial markers 204A-204C. For example, fiducial markers 204A-204C can be obstructed by tissue attached to skull 202 or the surgeon may not have the best line of sight of each of fiducial markers 204A-204C from the vantage point of human interface device 145, for example. Furthermore, even if each of fiducial markers 204A 204C is clearly visible, it can be difficult to ensure probe tip 210 engages the center of fiducial markers 204A-204C to most accurately register each point, or even if aligned with the center, advanced far enough to contact the fiducial marker without moving skull 202 or otherwise disturbing the patient.

In order to improve the accuracy of the registration process and ensure proper or desirable engagement between each of fiducial markers 204A-204C and probe tip 210, each of fiducial markers 204A-204C can include a sensory feedback device, such as light-up cap 214. Light-up cap 214 can provide a visual indicator when each of fiducial marker 204A 204C is accurately engaged, for example, when probe tip 210 engages the center of light-up cap 214. When probe tip 210 does engage the center of light-up cap 214, a button or switch can be actuated to activate a light source, such as a light bulb or light-emitting-diode. The light source can be a visual indication or sign to a surgeon or another operator of system 100 or another observer that probe tip 210 has engaged one of fiducial markers 204A-204C. In other examples, light-up cap 214 can provide other types of sensory signals, such as auditory signals, and can provide a communication signal to computing system 140 to indicate the engagement between the fiducial marker and probe tip 210 on a display of human interface device 145 (FIG. 1). For example, an image of patient 110 including fiducial markers 204A 204C shown in human interface device 145 can light up at each of fiducial markers 204A-204C as each fiducial marker is engaged.

Figure 3:
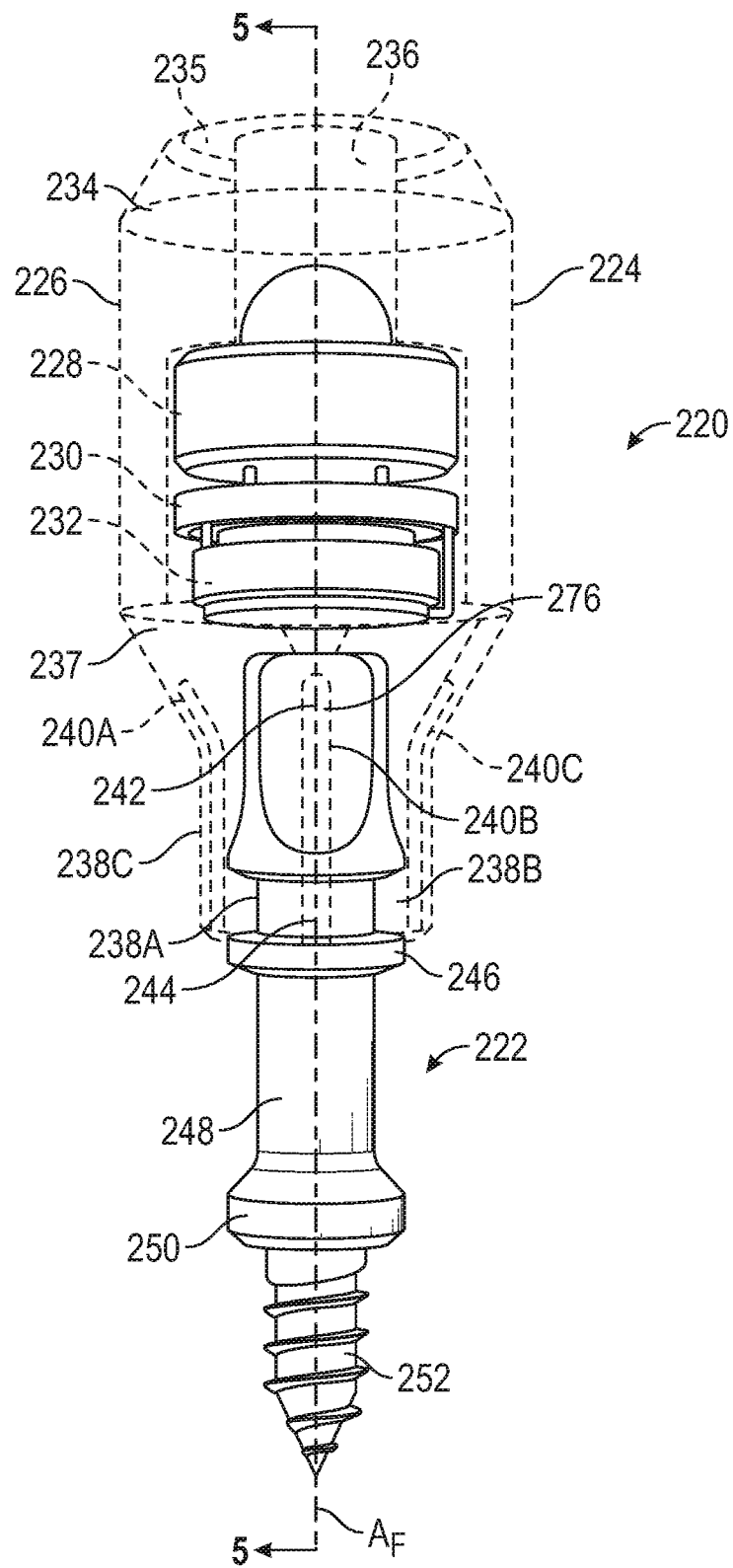
FIG. 3 is a side perspective view of a fiducial marker with feedback including a fastener and a light-up cap.
Figure 4:
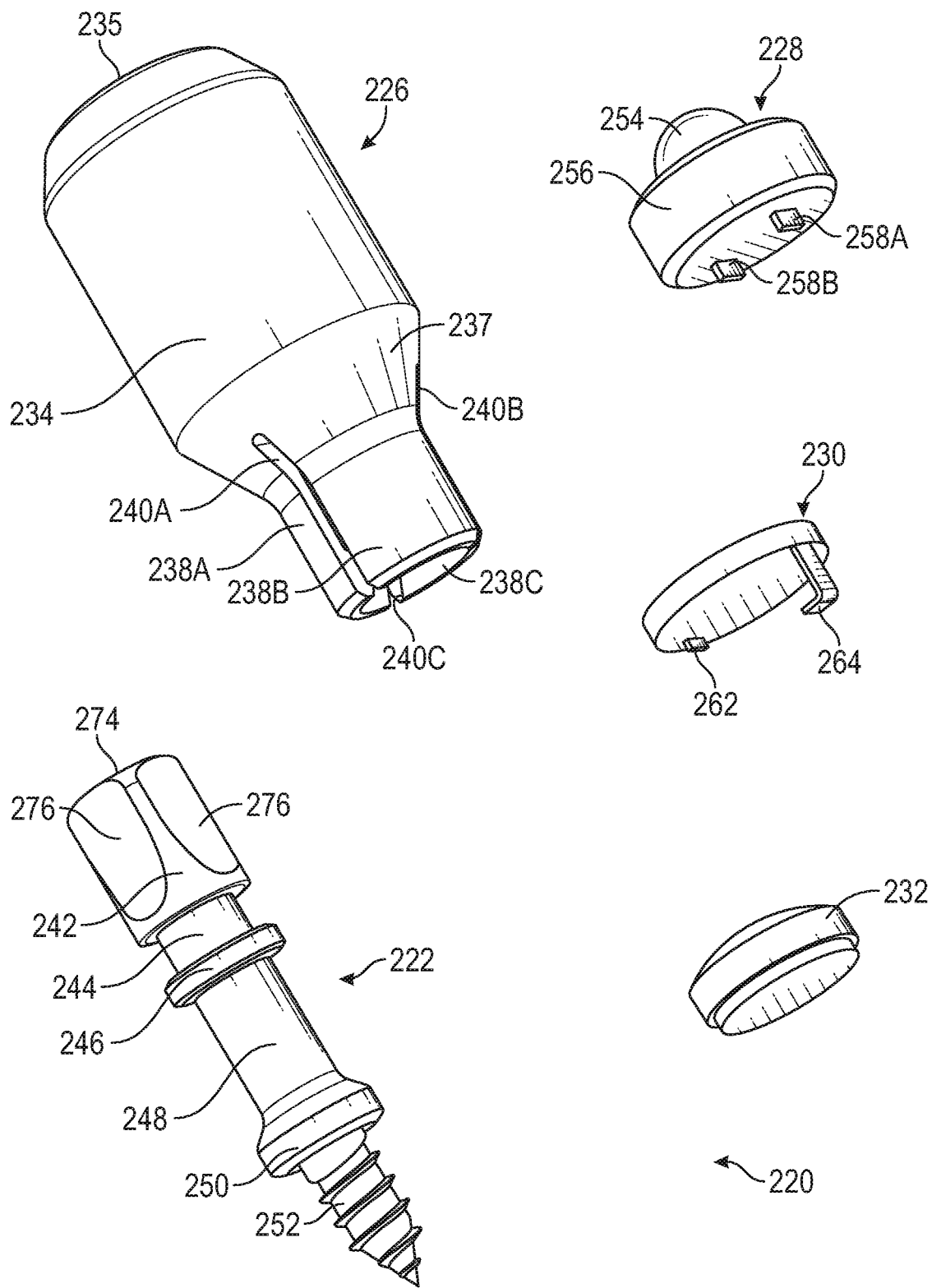
FIG. 4 is an exploded view of the fiducial marker of FIG. 3 showing a housing, a switch, a circuit board and a power source.

FIG. 3 is a side perspective view of fiducial marker 220 including fastener 222 and light-up cap 224. FIG. 4 is an exploded view of fiducial marker 220 of FIG. 3 showing housing 226, switch 228, circuit board 230 and power source 232 of light-up cap 224. FIGS. 3 and 4 are discussed concurrently unless specifically referenced. Light-up cap 224 can comprise an example of a feedback component.

Figure 5:
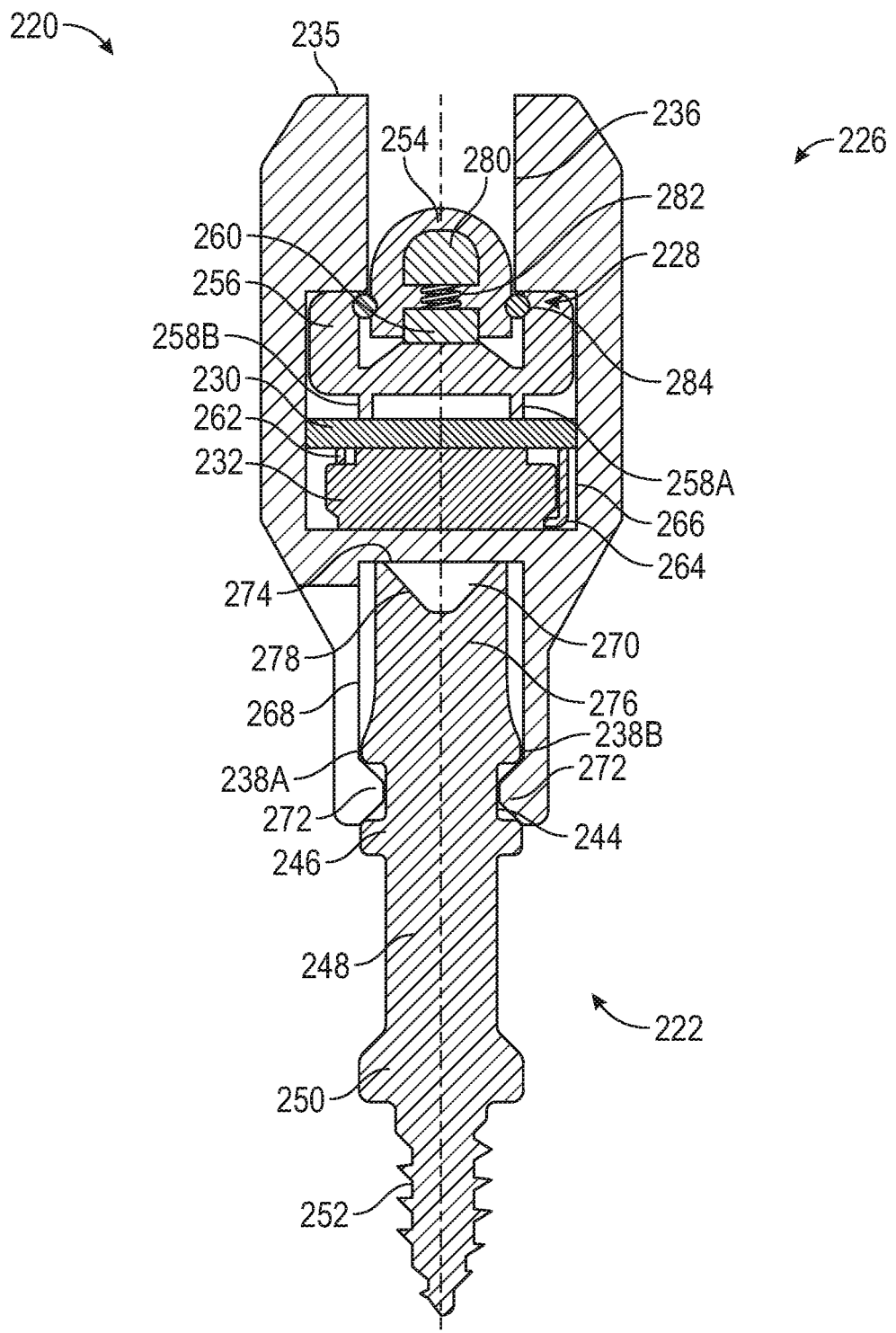
FIG. 5 is a cross-sectional view of the fiducial marker of FIG. 3 showing the location of the switch, circuit board and power source relative to an access port in the housing.

Light-up cap 224 can comprise housing 226, switch 228, circuit board 230 and power source 232. Housing 226 can be made of a translucent or transparent material such that components of light-up cap 224 can be viewed through housing 226. Housing 226 can comprise body 234, end surface 235, access port 236, transition portion 237, fingers 238A, 238B and 238C, and slots 240A, 240B and 240C. Fastener 222 can comprise head 242, channel 244, flange 246, shaft 248, shoulder 250 and anchor portion 252. Switch 228 can comprise button 254, body 256, contacts 258A and 258B and post 260 (FIG. 5). Circuit board 230 can include tab 262 and hook 264 for retaining power source 232.

Housing 226 of light-up cap 224 can be configured to couple to head 242 of fastener 222 such as to position switch 228 and access port 236 into axial alignment with fastener center axis $A_F$ of fastener 222. In the illustrated example of FIGS. 3-5, light-up cap 224 is configured to be attached to fastener 222 after fastener 222 is attached to a patient. In other examples, a light-up cap can be configured to be attached to a fastener before (or after) the fastener is attached to a patient. In such embodiments, features of the fastener used to attach the fastener to anatomy (e.g., facets 276) are not covered by the light-up cap. Additionally, in such embodiments, the light-up cap can be directly integrated into the head of the fastener. In such integrated examples, electronics can be embedded in a fastener. For example, near field technology, such as conductive metal, Radio Frequency Identification (RFID) tags, magnetic material, can be embedded in the head of the fastener. For such cases, probe tip 210 can be configured to include an appropriate sensor, such as a magnetic sensor or a conductivity/conduction sensor (e.g., current sensor) to measure the presence of magnetic material within the fastener or the presence of near field communication coil, respectively.

Figure 17:
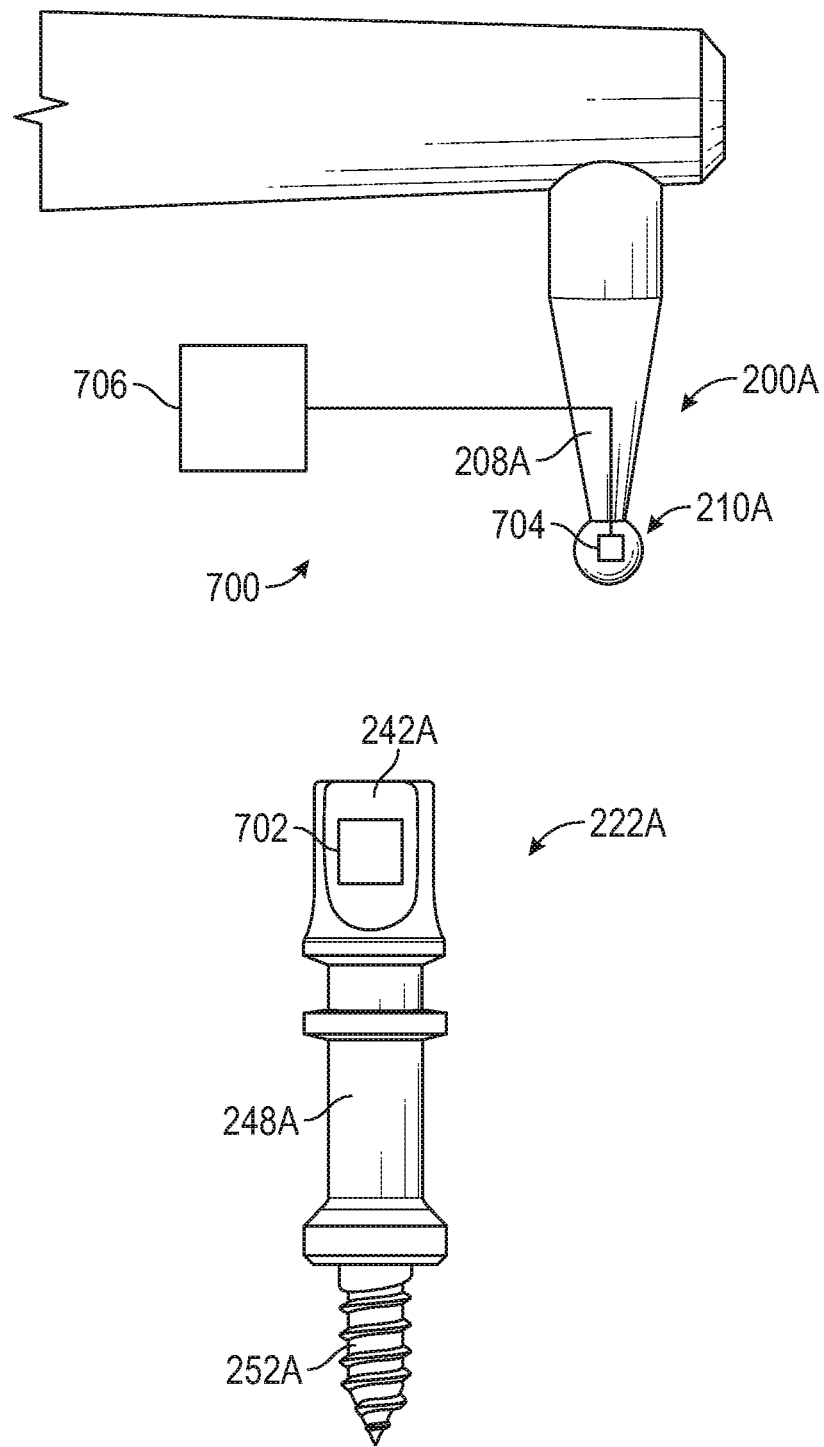
FIG. 17 is a schematic illustration of a system for sending input from a fiducial marker including an embedded sensor component for sensing by a pointer probe including an embedded sensor.

FIG. 17 is a schematic illustration of system 700 for sending input from fastener 222A including embedded sensor component 702 for sensing by pointer probe 200A including embedded sensor 704. Fastener 222A can comprise head 242A, shaft 248A and anchor portion 252A. Pointer probe 200A can include shaft 206A, probe extension 208A and probe tip 210A. Fastener 222A and pointer probe 200A can be configured similarly as fastener 222 and pointer probe 200, respectively, as described herein with the addition of sensor component 702 and sensor 704, respectively. System 700 can comprise sensor component 702, sensor 704 and controller 706. Controller 706 can comprise an element of computing system 140. In examples, controller 706 can be configured to communicate wirelessly or via wired connection with sensor 704.

In examples, sensor component 702 can comprise conductive material embedded in head 242A of fastener 222A and sensor 704 can comprise a current sensor. Thus, when sensor 704 contacts or approaches head 242A, a current can be generated and passing through sensor 702 and 704 and is registered by the controller 706. The magnitude of the current can be proportional to the amount of material forming sensor component 702 and is inversely proportional to the distance between probe tip 210A and head 242A, or otherwise influenced by the presence of sensor component 702. As such, sensor 704 will provide a baseline output when probe tip 210A is not in contact with fastener 222A, but will output a higher, or otherwise different, output when probe tip 210A contacts head 242A. This output signal can be registered by computing system 140 and can be used to provide feedback information, such as a physical or sensory indication of when a fiducial marker (e.g., fastener 222A) has been engaged in a correct location for registration by probe tip 210A.

In additional examples, sensor component 702 can comprise magnetic material embedded in head 242A of fastener 222A and sensor 704 can comprise a magnetism sensor. Thus, when sensor 704 contacts or approaches head 242A, a magnetic field generated by sensor component 702 can be emitted from fastener 222A into probe tip 210A. The magnitude of the magnetic field can be proportional to the amount of material forming sensor component 702 and is inversely proportional to the distance between probe tip 210A and head 242A. As such, sensor 704 will provide a baseline output when probe tip 210A is not in contact with fastener 222A, but will output a higher, or otherwise different, output when probe tip 210A contacts head 242A. This output signal can be registered by computing system 140 and can be used to provide feedback information, such as a physical or sensory indication of when a fiducial marker (e.g., fastener 222A) has been engaged in a correct location for registration by probe tip 210A.

In yet other examples, sensor component 702 can comprise an RFID tag or the like and sensor 704 can comprise a chip reader or the like.

In still other examples, sensor component 702 can be included in a sealed cap that can be fit onto head 242A. The cap can be configured similarly to cap 224, but with switch 228, circuit board 230 and power source 232 replaced by sensor component 702.

Further, information output from the feedback components discussed herein, such as light-up caps, conduction material, magnetic material and RFID tags, can be combined with force and torque information. In additional examples, switches (e.g., of light-up cap 224) and embedded electronics can be included with or in a single fastener for redundant information for security purposes, etc.

Returning to FIG. 2, fastener 222 can be attached to anatomy of a patient, such as by inserting anchor portion 252 into bone. In an embodiment, anchor portion can include one or more threads so as to be able to be threaded into bone. Shoulder 250 can be positioned adjacent anchor portion 252 and can provide a surface area for engaging bone to stop anchor portion 252 from being further advanced into bone. Shoulder 250 can also provide an anti-tilting feature to facilitate fastener 222 being positioned so that center axis $A_F$ can be perpendicular to a surface of the bone to which it is attached.

Shaft 248 can extend from shoulder 250 along center axis $A_F$. Shaft 248 can provide clearance for head 242, such as above tissue of the patient. In examples, shaft 248 can be in the range of approximately 1 cm to approximately 3 cm in length. Flange 246 can extend from shaft 248 to, for example, provide a feature or surface for engaging housing 226. In an example, flange 246 can extend radially from shaft 248 to provide a flat distal surface for engaging fingers 238A-238C of housing 226.

Head 242 can be attached to an end of shaft 242 proximal to flange 246 so as to form channel 244 between head 242 and flange 246. Facets 276 (FIGS. 4 and 5) of head 242 can be located proximally of channel 244. Facets 276 can facilitate insertion into tissue or bone and assembly with light-up cap 224. For example, facets 276 can engage working surfaces of a tool, such as a wrench, to facilitate rotation of fastener 222. In examples, head 242 can include four of facets 276 to form a square or rectilinear head, though in other examples other numbers of facets can be included to, for example, form a hex head, etc. Proximal end surface 274 can comprise the proximal-most portion of head 242 and fastener 222, and can be configured to engage housing 226.

In an example, the distal-most end of housing 226 can comprise fingers 238A-238C. Fingers 238A-238C can be separated by slots 240A-240C. Fingers 238A-238C can be spread apart to fit over head 242 to hold housing 226 in engagement with fastener 222. Fingers 238A-238C can have a thickness that is thin enough to permit flexion, but thick enough to hold housing 226 to fastener 222. In examples, the distal-most end of housing 226 can comprise one or more threads configured to engage corresponding threading on an instrument or fastener. Housing 226 can include transition portion 237 that can connect fingers 238A 2380 to body 234. Transition portion 237 can comprise a flared or conical portion that extends radially from fastener center axis $A_F$ to increase the diameter of housing 226 at body 234 greater than the diameter at fingers 238A-238C. Body 234 can, for example, have a larger diameter than fingers 238A-238D in order to provide space to accommodate switch 228, circuit board 230 and power source 232. Access port 236 can be located in end surface 235 of housing 226 to provide access to switch 228, circuit board 230 and power source 232 within housing 226.

With reference to FIG. 4, power source 232 can comprise a conventional battery including an electrochemical cell, such as an alkaline or zinc-manganese battery. Power source 232 can comprise other types of power-providing devices, such as a rechargeable battery or a large capacitor. Power source 232 can be mechanically coupled to circuit board 230, such as by hook 264. Hook 264 may also provide a terminal electrically connecting to the positive or negative side of power source 232. Hook 264 can be shaped and configured to push power source 232 against tab 262 to retain power source 232 against circuit board 230. Tab 262 may also provide a terminal electrically connecting to the positive or negative side of power source 232.

Circuit board 230 can comprise a controller for light-up cap 224. Circuit board 230 can include circuitry that can direct power from power source 232 to switch 228. As is discussed with reference to FIG. 13 circuit board 230 can include various other components for operating switch 228, such as logic for controlling the color of one or more light-emitting sources, such as based on the number of times switch 228 is actuated, and a transmitter for communicating with computing system 140 (FIG. 1). For example, the first time switch 228 is activated, light-emitting source 280 (FIG. 5) can emit a first color, the second time switch 228 is activated, light-emitting source 280 can emit a second color different from the first color, and the third time switch 228 is activated, light-emitting source 280 can emit a third color different from the first and second colors. The transmitter can include circuitry to perform wireless communications, such as low-energy Bluetooth, near-field communication (NFC), or IEEE 802.11 (Wi-Fi).

Switch 228 can comprise elements for selectively activating a light-emitting device included therein. Contacts 258A and 258B can extend from body 256 of switch 228 to electrically connect with circuit board 230. Contacts 258A and 258B can provide power coupling and communication between switch 228 and circuit board 230. Button 254 can extend from body 256 and can house other elements of switch 228. For example, as discussed with reference to FIG. 5, button 254 can house light-emitting devices or other sensory indicators.

FIG. 5 is a cross-sectional view of fiducial marker 220 of FIG. 3 showing the location of switch 228, circuit board 230 and power source 232 relative to access port 236 in housing 226. Housing 226 can also comprise compartment 266, socket 268, prong 270 and tabs 272. Head 242 of fastener 222 can further comprise proximal end surface 274, facets 276 and divot 278. Button 254 can further comprise light-emitting source 280, spring 282 and seal 284.

Housing 226 can comprise a platform for holding button 254 of switch 228. Button 254 can comprise a translucent or transparent lens through with light waves from light-emitting source 280 can pass. Likewise, housing 226 can be translucent or transparent so that light waves from light-emitting source 280 can pass therethrough. The light waves can be generated when button 254 is depressed into housing 226 to provide an indication that pointer probe 200 has accurately engaged fastener 222 so that computing system 140 (FIG. can record the location of fastener 222.

Housing 226 can be slid onto head 242 of fastener 222. Head 242 can be pushed into socket 268 by an operator of fiducial marker 220, such as a surgical technician or a surgeon. Under such force, fingers 238A 238C can deflect radially outward relative to center axis $A_F$ to permit tabs 272 to contacts facets 276. An operator can continue to push housing 226 onto head 242 such that tabs 272 slide along facets 276 until tabs 272 reach channel 244. Tabs 272 can be sized to seat between head 242 and flange 246 to hold housing 226 on fastener 222. In an embodiment, the lengths of fingers 238A 238C can be such that tabs 272 will center on channel 244 when proximal end surface 274 of head 242 engages flush with the top of socket 268. In such an arrangement, housing 226 can be axially immobilized relative to central axis $A_F$, but can rotate circumferentially about center axis $A_F$.

Prong 270 can be included on housing 226 to seat within divot 278. Divot 278 can be configured and shaped to receive probe tip 210 of pointer probe 200 to perform a registration procedure without light-up cap 224, Divot 278 can comprise a semi-spherical depression or a hex-type socket. Prong 270 can comprise a projection to mate with divot 278 to, for example, facilitate seating and axial alignment between fastener 222 and housing 226 along center axis $A_F$. In examples, prong 270 can be omitted from housing 226.

Power source 232 can be positioned in compartment 266, such as at the bottom or distal-most portion of compartment 266. Circuit board 230 can be stacked on top of power source 232 and coupled thereto by tab 262 and hook 264. Switch 228 can be stacked on top of circuit board 230 and coupled thereto by contacts 258A and 258B.

Access port 236 can be centered on end surface 235 and can be centered over switch 228. Configured as such, button 254 can protrude into access port 236, while housing 256 is located within compartment 266. The shape and location of access port 236 can position the center of button 254 on center axis $A_F$. In embodiments, the height of compartment 266 can correspond to the stacked height of power source 232, circuit board 230 and housing 256 including contacts 258A and 258B, tab 262 and hook 265. Likewise, the diameter of compartment 266 can correspond to the diameters of power source 232, circuit board 230 and housing 256, Configured as such, power source 232, circuit board 230 and switch 228 can be retained within compartment 266 with minimal movement, while button 254 is free to be axially displaced along center axis $A_F$. Access port 236 can center engagement with button 254 from probe tip 210, for example.

Figure 6:
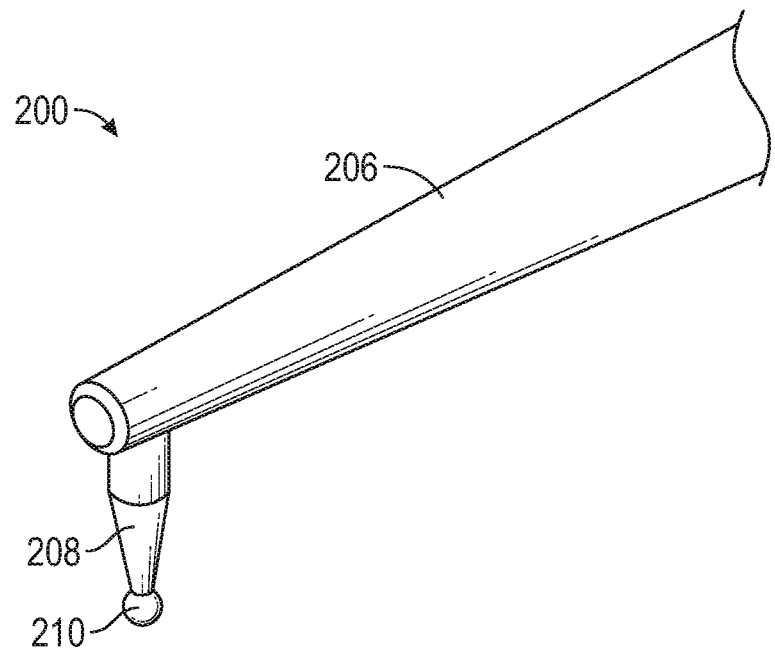
FIG. 6 is a perspective view of the pointer probe of FIG. 2 showing a probe tip.

FIG. 6 is a perspective view of pointer probe 200 of FIG. 2 showing probe tip 210. Pointer probe 200 can also comprise shaft 206 and extension 208. Pointer probe 200 can comprise an instrument, such as one of surgical instruments 125 (FIG. 1) compatible with robotic arm 120 and surgical system 100 of FIG. 1. Pointer probe 200 can comprise an instrument of known geometry relative to robotic arm 120 that can be used to perform registration procedures and methods with fiducial markers 204A 204C and fiducial marker 220. Probe tip 210 can be configured to engage with fiducial markers 204A-204C, fiducial marker 220 and other fiducial markers. Probe tip 210 can comprise a ball-shaped body that can seat against curved surfaces of various fiducial markers, such as divot 278 (FIG. 5) or seat 318 (FIG. 9). The diameter of probe tip 210 can be sized to fit within access port 236 (FIG. 5) of housing 226. For example, the diameter of a ball of probe tip 210 can be sized to slip fit within access port 236 such that probe tip 210 and extension 208 self-center within access port 236 to improve the precision of the registration process. Extension 208 can be tapered or necked-down to a size smaller than the diameter of a ball of probe tip 210 to facilitate insertion of probe tip 210 into access port 236, and extension 208 can have sufficient length to ensure probe tip 210 can extend through access port 236 to reach button 254, as are discussed with reference to FIG. 8.

Figure 7:
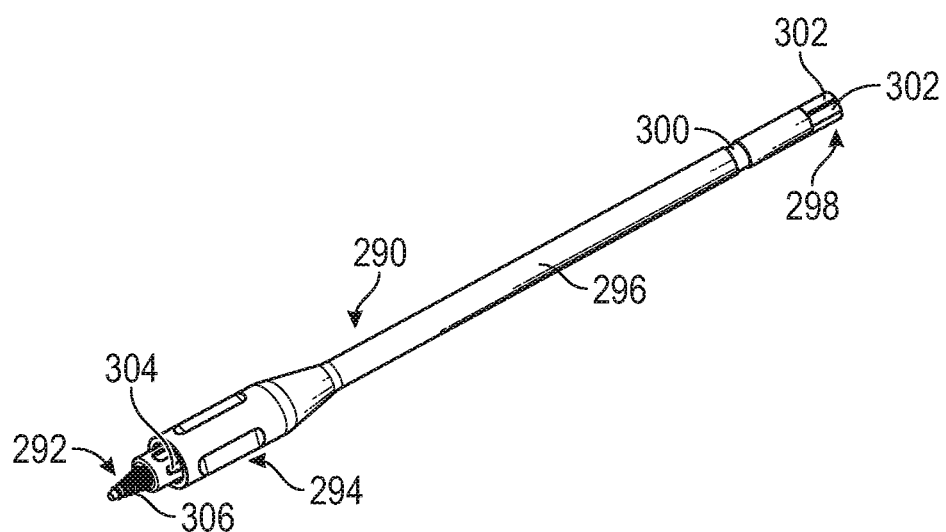
FIG. 7 is a perspective view of a driver configured for use with the robotic arm of FIG. 2 and a fastener inserted into the driver.

FIG. 7 is a perspective view of a driver 290 configured for use with robotic arm 120 of FIG. 2 and fastener 292 inserted into socket 294 of driver 290. Driver 290 can comprise an instrument, such as one of surgical instruments 125 (FIG. 1) compatible with robotic arm 120 and surgical system 100 of FIG. 1, or can be used in combination with a manual driver instrument. Driver 290 can comprise shaft 296, which can include drive input end 298 and socket 294. Drive input end 298 can couple to robotic arm 120 and can include channel 300 in which retention means of robotic arm 120 can be received to prevent driver 290 from being displaced from robotic arm 120. Drive input end 298 can also include facets 302 for engaging a rotational drive socket of robotic arm 120. In other embodiments, driver 290 can be used in conjunction with a manual driver handle coupled to drive input end 298. As such, robotic arm 120 or manually-generated power can be configured to impart rotation motion to driver 290 along the longitudinal length of driver 290 via transmission of force to facets 302. Rotation of driver 290 can additionally cause rotation of socket 294 to rotate fastener 292. Fastener 292 can include head 304 that can be inserted into socket 294. Head 304 can include external facets that can mate with internal facets of socket 294 such that rotation of socket 294 can be imparted to fastener 292. Fastener 292 can include threaded shaft 306. Rotation of fastener 292 via driver 290 can cause threaded shaft 306 to be inserted into anatomy of a patient, such as bone. Head 304 of fastener 292 can include any number of facets, such a four like fastener 222. As such, driver 290 can be configured to drive fastener 222 via engagement with facets 276.

Figure 8:
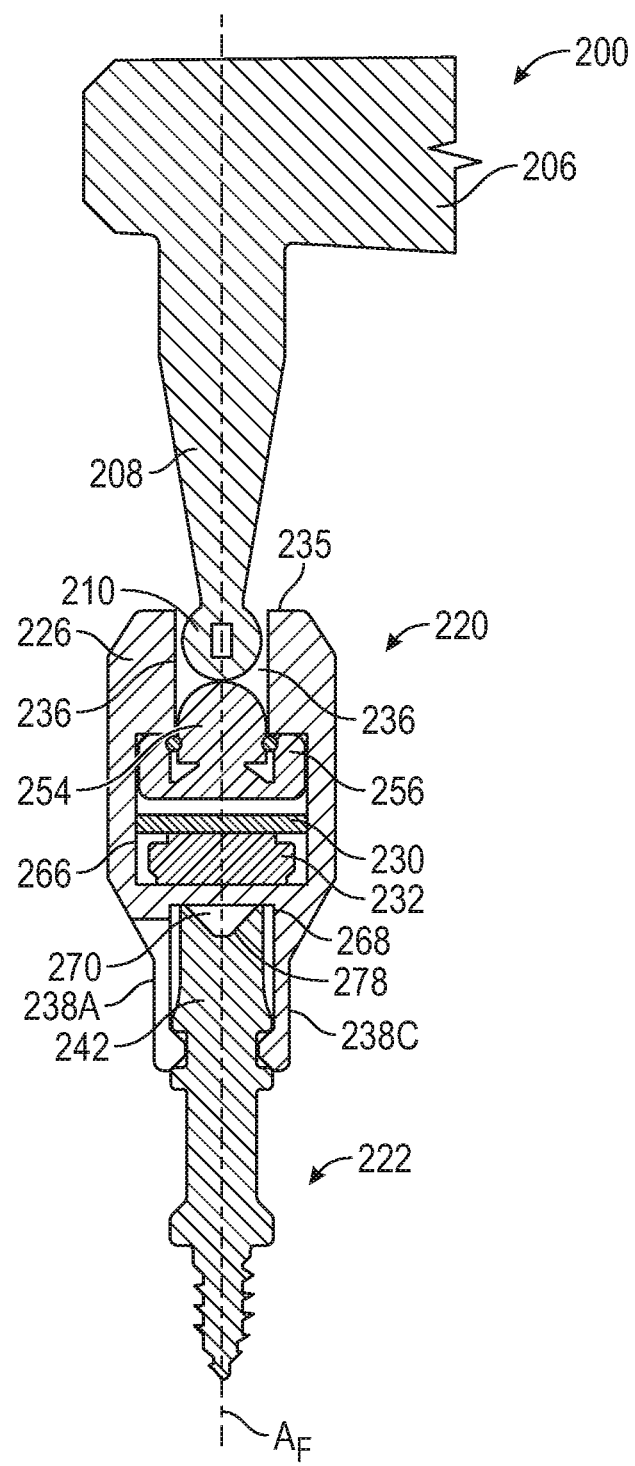
FIG. 8 is a side cross-sectional view of the fiducial marker of FIG. 3 showing the probe tip of the pointer probe inserted into the access port of the housing.
Figure 9:
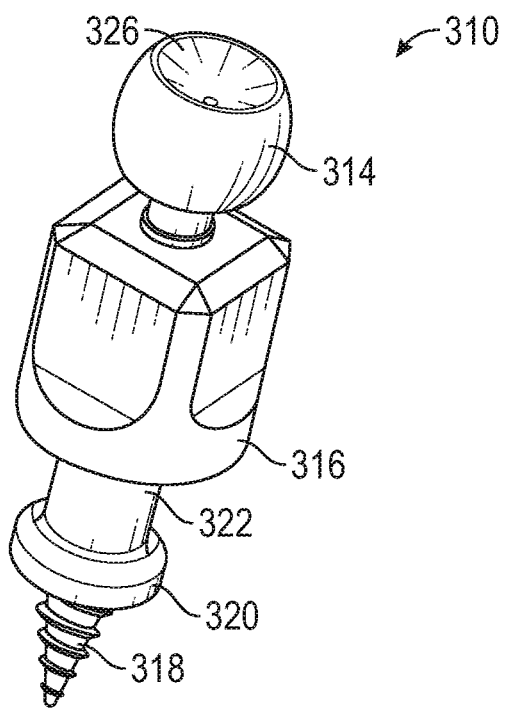
FIG. 9 is a perspective view of another embodiment of a fastener for a fiducial marker that can be used with a light-up cap.

FIG. 8 is a side cross-sectional view fiducial marker 220 of FIG. 3 showing probe tip 210 of pointer probe 200 inserted into access port 236 of housing 226. Extension 208 can be tapered or necked-down to a size smaller than the diameter of a ball of probe tip 210 to facilitate insertion of probe tip 210 into access port 236. Likewise, extension 208 can be of sufficient length to receive substantially all of probe tip 210, so that the sides of probe tip 210 can be tangent to walls of access port 236. As mentioned, access port 236 can be centered over button 254 to center probe tip 210 on fiducial marker 220. The depth of access port 236 from end surface 235 can be long enough to receive substantially all of the ball of probe tip 210 to ensure that sides of probe tip 210 engage the walls of access port 236. The diameter of access port 236 can be slightly larger than the diameter of probe tip 210 to that probe tip 210 can engage the walls of access port 236 and center probe tip 210 on fastener center axis $A_F$. The relationship, e.g., dimensions, of probe tip 210 relative to probe shaft 206 can be stored in computing system 140 (FIG. 1). For example, extension 208 can extend perpendicularly from the axis of probe shaft 206 at a known distance, and probe tip 210 can be located a known distance from robotic arm 120 (FIG. 2). As such, when probe tip 210 engages button 254, the location of fastener 222 can be correlated back to a location in a coordinate system for surgical area 105 of surgical system 100 (FIG. 1) based on the known geometry of robotic surgical arm 120 or the use of tracking elements 170.

Figure 10:
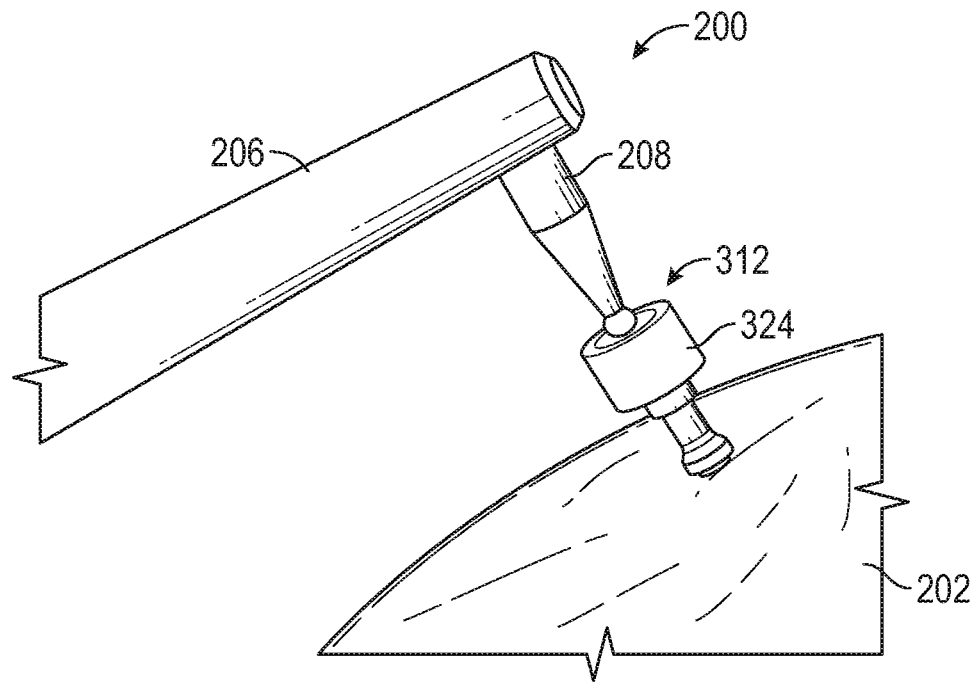
FIG. 10 is a perspective view of the pointer probe engaging a light-up cap configured for use with the fastener of FIG. 9.

FIG. 9 is a perspective view of fastener 310 for a fiducial marker that can be used with light-up cap 312 of FIG. 10. FIG. 10 is a perspective view of pointer probe 200 engaging light-up cap 312 configured for use with fastener 310 of FIG. 9. FIGS. 9 and 10 are discussed concurrently.

Fastener 310 can be similar to fastener 222 except rather than channel 244 being located below or distal to head 242, ball head 314 is located above or proximal to head 316. Fastener 310 can comprise similar components as fastener 222, such as anchor portion 318, shoulder 320, shaft 322 and head 316, which can be analogous to anchor portion 252, shoulder 250, shaft 248 and head 242, respectively. Head 316 can be connected directly to shaft 322 without the presence of flange 246. Head 316 can include facets similar to facets 276 for engaging a tool to rotate and implant fastener 310. Ball head 314 can provide a separate anchor point for connection with light-up cap 312. For example, flexible fingers of housing 324 of light-up cap 312 can flex around ball head 314 to provide coupling. Ball head 314 can include seat 326 for receiving probe tip 210. Housing 324 can comprise features to engage seat 326 to facilitate coupling and immobilization of housing 324 relative to fastener 326. Housing 324 can extend completely over ball head 314 to engage facets of head 316 to prevent pivoting of light-up cap 312 about ball head 314 and rotating of light-up cap 312 relative to shaft 322. As such, housings for the fiducial marker caps, such as housings 226 and 324, described herein can be configured to attach to different components of surgical system 100, including pointer probe 200 as shown in FIG. 11.

Figure 11:
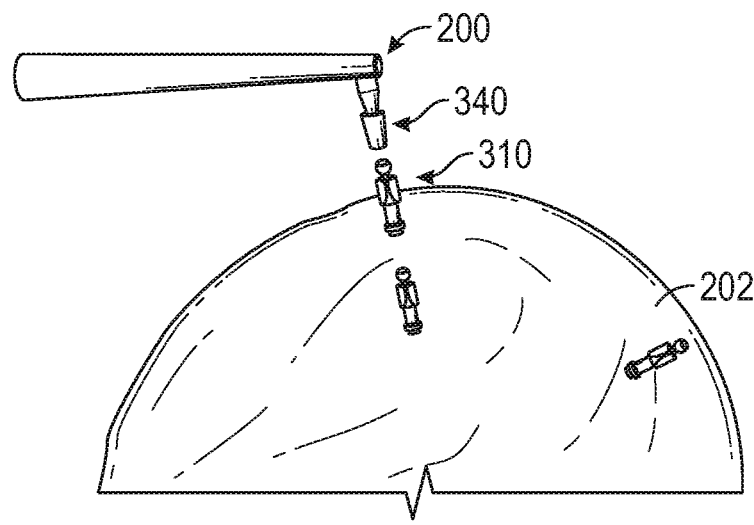
FIG. 11 is a perspective view of an embodiment of a light-up probe cap that can be used in conjunction with fiducial marker fasteners.
Figure 12:
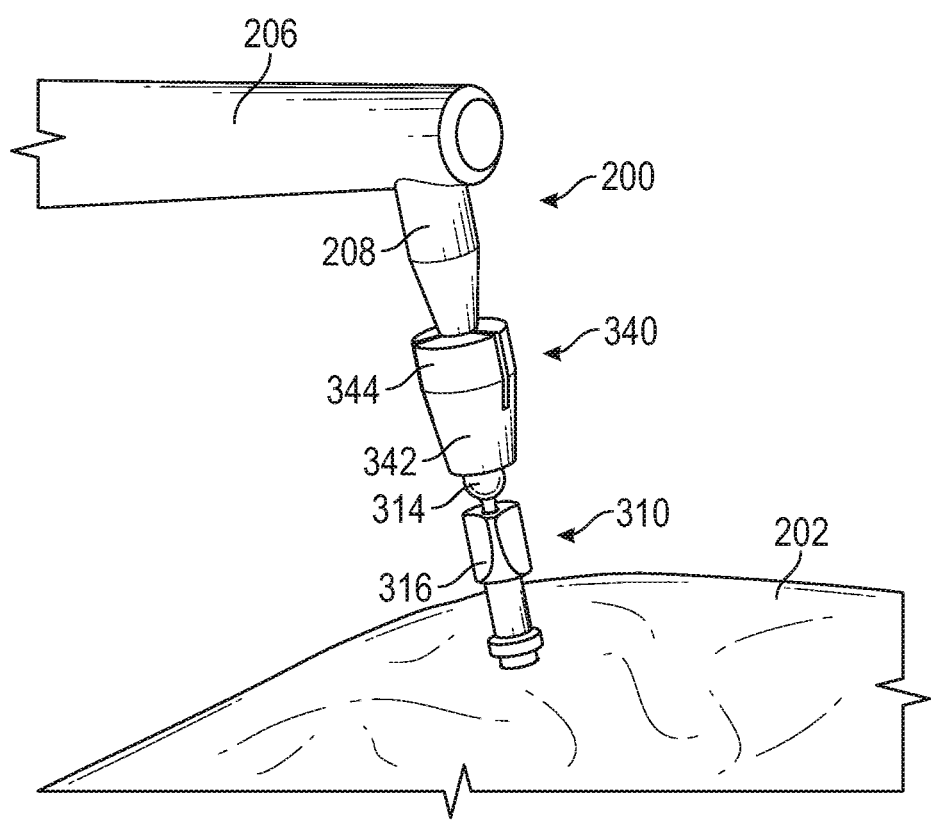
FIG. 12 is a perspective view of the light-up probe cap of FIG. 11 engaging a head of a fiducial marker fastener.

FIG. 11 is a perspective view light-up probe cap 340 that can be used in conjunction with fiducial marker fastener 310, or other fasteners. FIG. 12 is a perspective view of light-up probe cap 340 of FIG. 11 engaging head 314 of fiducial marker fastener 310. FIGS. 11 and 12 are discussed concurrently.

Fiducial marker fastener 310 can include the same or similar components as fastener 310 identified and discussed with reference to FIGS. 9 and 10. Light-up probe cap 340 can function similarly as light-up cap 220 of FIGS. 3-5, but can be configured to attach to pointer probe 200 rather than a fiducial marker. Light-up probe cap 340 can include the same components as light-up cap 220 except rather than housing 226 being configured to attach to head 242, housing 342 can be configured to attach to probe tip 210. Housing 342 can include fingers 344 shaped to wrap around the ball shape of probe tip 210 and engage flush with extension 208.

Figure 13:
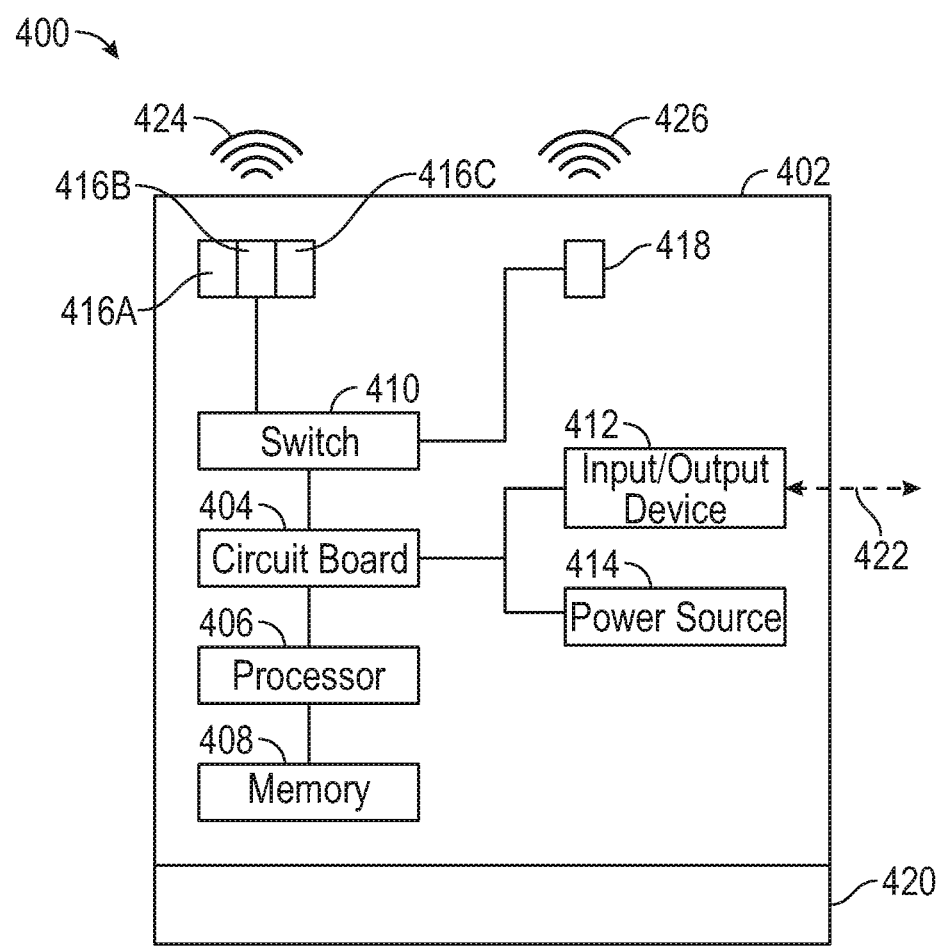
FIG. 13 is a block diagram illustrating components of a sensory feedback fiducial marker cap.

FIG. 13 is a block diagram illustrating components of sensory feedback fiducial marker cap 400. Sensory feedback fiducial marker cap 400 can comprise housing 402, circuit board 404, processor 406, memory 408, switch 410, input/output (I/O) device 412, power source 414, light sources 416A, 416B and 416C and wave generator 418. Housing 402 can be attached or integral with fiducial marker fastener 420.

Housing 402 can comprise a structural component to hold and support other components of fiducial marker cap 400. Housing 402 can be integral with a fiducial marker fastener, such as fasteners 222 and 310. However, in other examples, housing 402 can include a compartment for receiving the components of fiducial marker cap 400, as well as a socket, e.g., socket 268, for receiving another component of surgical system 100, such as probe tip 210 or the head of a fiducial marker fastener, such as heads 242 and 314, and an access port, e.g., access port 236, for receiving the other of the probe tip of the fastener head. Housing 402 can be made of a medical grade plastic material, or can be made of other medical grade materials, such as stainless steel. Housing 402 can be made of a transparent or translucent material to facilitate transmission of light through housing 402 to improve visibility of any light sources disposed in or on housing 402, such as light sources 416A-416C.

Circuit board 404 can comprise a structural component for coupling electrical components of fiducial marker cap 400. For example, circuit board 404 can comprise a silicon wafer into which electrical couplings are attached for coupling switch 410, processor 406, memory 408 and the like.

Processor 406 can comprise an integrated circuit that controls operation of components of fiducial marker cap 400, such as switch 410, 110 device 412 and light sources 416A, 416B and 416C.

Memory 408 can comprise any suitable storage device, such as non-volatile memory, magnetic memory, flash memory, volatile memory, programmable read-only memory and the like. Memory 408 can include instructions stored therein for processor 406 to control operation of fiducial marker cap 400. For example, memory 408 can include instructions for lengths of time for which to activate light sources 416A-416C when switch 410 is activated, for colors of light sources 416A-416C and the sequence in which to activate light sources 416A-416C.

Switch 410 can comprise a an on/off switch for providing power from power source 414 to light sources 416A-416C. Switch 410 can comprise an "alternate action" switch or a "momentary action" switch when transitioning between open or closed states. In alternate action switches, a switch can be flipped for continuous "on" or "off" operation. In momentary action switches, a switch can be activated or engaged for "on" operation and released for "off" operation. As such, switch 410 can comprise a toggle switch, a knife switch, a relay or a push-button switch. Switch 410 can include means, such as spring 282, for returning switch 410 to a released or "off" position from an engaged or "on" position.

I/O device 412 can comprise one or more devices for receiving input from surgical system 100 or providing an output to surgical system 100 via signal 4220. I/O device 412 can provide signal 422 to computing system 140 of surgical system 100 indicating the state of switch 410 or light sources 416A-416C. Computing system 140 can thereafter, for example, display on human interface device 145, such as a video display monitor, an indication of when fiducial marker cap 400 has been engaged. Computing system 140 can also be configured to provide an auditory signal or alarm for when fiducial marker cap 400 has been engaged after receiving signal 422. Signal 422 can additionally comprise or include data relating to the number of times or the length of time that switch 410 has been engaged. I/O device 412 can receive signal 422 from computing system 140 for storing information on memory 408 or providing information to processor 406 for operating switch 410 and light sources 416A-416C. For example, computing system 140 can program fiducial marker cap 400 for the length of time to activate light sources 416A-416C, the colors for activating light sources 416A-416C, or sounds to produce with I/O device 412. In examples, I/O device 412 can communicate using wireless communications signals, such as Bluetooth, WiFi, Zigbee, infrared (IR), near field communication (NFC), 3GPP or other technologies.

Power source 414 can comprise an energy storage device such as a battery including an electrochemical cell, such as an alkaline or zinc-manganese battery. Power source 414 can be rechargeable.

Light sources 416A-416C can comprise one or more devices for producing light waves 424, such as incandescent light bulbs, light-emitting-diodes and the like. In examples, light sources 416A-416C can comprise separate light emitting devices integrated into a single device and each can be configured for emitting a different color or wavelength of light. In examples, light sources 416A-416C can comprise a single light-emitting device configured for emitting a plurality of different colors or wavelengths. As discussed herein, light sources 416A-416C can provide visual indications of when fiducial markers are engaged by a robotic surgical system when performing a registration process. For example, light sources 416A-416C can be configured to emit orange, yellow and green light, respectively. In an example, the first time switch 410 is engaged, light source 416A can light up orange, the second time switch 410 is engaged, light source 416B can light up yellow and light source 416A can shut off, and the third time switch 410 is engaged, light source 416C can light up green and light source 416B can shut off. As such, an operator can confirm that three consecutive engagements of fiducial marker cap 400 have been completed. In other example, a light source can be configured to light up red to indicate a condition of fiducial marker cap 400, such as a loss of communication or a malfunction of switch 410. In other examples, fiducial marker caps 400 attached to different fiducial marker fasteners can be configured to each light up a different color such that a surgeon can view a location-specific color for each fiducial marker.

Wave generator 418 can include or comprise a device such as for making wave 426, such as a sound wave or a vibration wave. In an example, wave generator 418 can comprise an auditory device, such as a speaker or amplifier for producing an auditory signal or sound to indicate that fiducial marker cap 400 has been engaged. In other examples, wave generator 418 can comprise tactile device, such as a reciprocating or oscillating device, for producing a vibration that can be felt by a surgeon or operator of system 100. For example, wave 426 can communicate with a device worn by a surgeon at computing system 140 that can vibrate when receiving wave 426.

Sensory feedback fiducial marker cap 400 can thus be configured to provide one or more different types of sensory feedback to a surgeon or operator of surgical system 100 (FIG. 1). The sensory feedback can comprise visual, auditory or tactile stimulus to the surgeon or operator. The sensory feedback can be electrically generated, such as with power from power source 414. The sensory feedback can take on the form of a light wave, a sound wave, a vibration wave, or an electrical or communication signal. The sensory feedback can provide an indication or confirmation that probe tip 210 of robotic surgical arm 120 (FIG. 2) has engaged a fiducial marker, such as fiducial marker fastener 222 or 310. Receipt of the sensory feedback can allow the surgeon or operator to know that pointer probe 200 is in position for a location reading to be taken by computing system 140 for the location of the fiducial marker in a coordinate system for surgical system 100, such as with a tracking element 170.

Sensory feedback fiducial marker cap 400 and the other fiducial marker caps described herein can be disposable or can be reusable. For example, housings 226 and 342 can be separable from fasteners so that each component can be cleaned. Housing 226 can include seal 284 to prevent cleaning fluid from reaching electrical components within housing 226. In examples, the various housings described herein can include separable components such that the electrical component located therein can be accessed, such as to change power source 414. In other examples, power source 414 can be wirelessly charged through a housing. However, in order to reduce the cost of manufacturing each sensory feedback fiducial marker cap described herein, they can be configured as one-time-use items.

Figure 14:
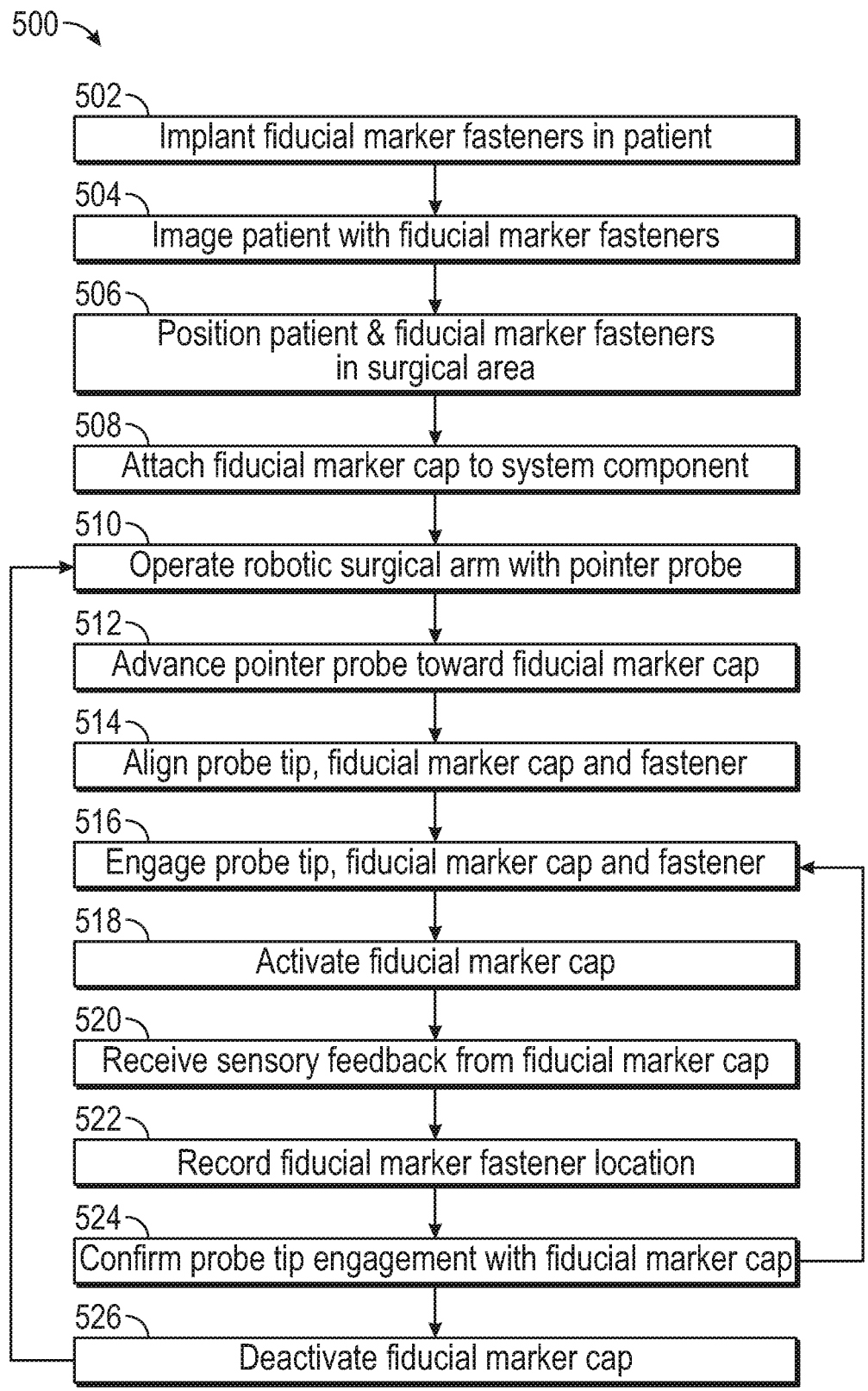
FIG. 14 is a flow chart illustrating steps of a method for registering an anatomy to a robot-assisted surgical system in accordance with the systems and methods relating to fiducial markers with feedback described herein.

FIG. 14 is a flowchart illustrating actions or steps of method or technique 500 for registering an anatomy to a robot-assisted surgical system, such as surgical system 100 of FIG. 1, in accordance with the systems and methods relating to fiducial markers with feedback described herein.

At step 502, fiducial marker fasteners, such as fasteners 222 and 310 can be implanted into or onto a patient, such as patient 110 (FIG. 1). For example, fasteners 222 can be threaded into bone of skull 202 of patient 110. A plurality of fasteners 222, for example, can be implanted into skull 202 at anatomic locations to mark the topology of skull 202 and anatomy, tissue or organs inside of skull 202. Fasteners 222 can include sensory feedback fiducial marker caps described herein that are integrated into the fastener. However, in various embodiments, the sensory feedback fiducial marker caps can be attached to a component of surgical system 100, such as fasteners 222 or pointer probe 200, as a separate component from the fastener.

At step 504, the patient with the implanted fiducial marker fasteners can be imaged to obtain imaging of the anatomy of the patient including the implanted fiducial marker fasteners. Multiple images can be obtained at different angles to show the anatomy relative to a plurality of fiducial marker fasteners in order to develop a three-dimensional map of the anatomy of the patient. The imaging can be obtained from any suitable medical imaging system, such as x-ray imaging, computed tomography (CT) imaging, magnetic resonance imaging, (MRI), ultrasonic imaging, sonographic imaging and the like. The imaging can be stored in surgical system 100, such as at computing system 140 and can be viewed on human interface device 145.

At step 506, the patient and the fiducial marker fasteners can be moved into an operating room or surgical area, such as surgical area 105 (FIG. 1). The patient can be positioned such that the anatomy where the fiducial marker fasteners are attached are accessible by surgical arm 120. As such, the patient can be positioned within a virtual coordinate system for surgical system 100.

At step 508, one or more fiducial marker caps can be attached to a system component. For example, in an embodiment, light-up probe cap 340 can be attached to probe tip 210 of pointer probe 200 for use with multiple fiducial marker fasteners. In other examples, multiple light-up caps 224 can be attached to multiple fasteners 222, or multiple light-up caps 340 can be attached to multiple fasteners 310. In some situations, it can be advantageous or desirable to separately attach multiple light-up or sensory caps to fasteners. For example, suitable imaging of the anatomy of the patient can be obtained without the light-up or sensory caps and any interference that may be caused therefrom. For example, electrical components of cap 400 may cause electrical interference with the imaging system, or housing 226 may interfere with visibility of head 242 of fastener 222 in the Obtained images.

At step 510, pointer probe 200 can be attached to robotic surgical arm 120. Robotic surgical arm 120 can be operated, such as by causing rotation about axes 216A-216D using computing system 140, to bring pointer probe 200 proximate to one of the fiducial marker fasteners. In another example, a separate pointer probe instrument can be tracked by an optical tracking system to enable the registration process. In this example, robotic surgical arm 120 can be separately registered into the same coordinate system using the optical tracking system. A separate tracked pointer probe instrument can function in a similar manner to pointer probe 200, while the optical tracking system tracks location and orientation from tracking markers affixed to the tracked pointer probe instrument.

At step 512, pointer probe 200 can be advanced toward a fiducial marker cap, or a fiducial marker fastener. For example, robotic surgical arm 120 can position pointer probe 200 so that probe tip 210 is positioned opposite a surface of a fiducial marker cap, such as end surface 235 of cap 220 (FIG. 3), including a switch or an access opening for a switch. In other examples, robotic surgical arm 120 can position a fiducial marker cap, such as cap 340 (FIG. 12) attached to probe tip 210 opposite a fiducial marker head, such as head 242 or 314.

At step 514, probe tip 210, the fiducial marker cap and the fiducial marker fastener can be aligned. In an example, probe tip 210 of pointer probe 200 can be centered on a fiducial marker cap housing. In order to facilitate the centering, probe tip 210 can be positioned within an access port of cap housing, such as access port 236. The geometry of the access port and the location of the access port in the housing can center probe tip 210 on the fiducial marker fastener. In other examples, probe tip 210 with cap 340 can be centered on head 314 of fastener 310.

At step 516, robotic surgical arm 120 can be manipulated to activate a switch within the fiducial marker cap. In an example, probe tip 210 can engage a switch within the fiducial marker cap, such as cap 220. In another example, a head of a fiducial marker fastener can engage a switch within the fiducial marker cap, such as cap 340. Reaction forces applied to probe tip 210 can be managed by computing system 140. In some typical operating conditions, when a force is applied to probe tip 210, arm 120 can be instructed to move in the direction of the force. Thus, for example, if probe tip 210 engaged a switch within a fiducial marker cap, probe tip 210 would be programmed to react by moving away from the fiducial marker cap. However, during the registration procedure, it might be advantageous to avoid such a rebound. As such, computing system 140 can be put in a registration mode where a force sensor could be used to detect the rebound and send a command signal to computing system 140 to not take into account this information and move arm 120. Likewise, lateral forces applied to probe tip 210 can be managed by computing system 140 during the registration process. For example, if probe tip 210 unintentionally touches walls of the fiducial marker cap, e.g., walls of access port 236 of housing 226 in FIG. 3, probe tip 210 would ordinarily be programmed to rebound, as described above, and could then engage the opposite wall of the fiducial marker cap causing a resonance effect where probe tip 210 could be continuously moved between opposing walls of the access port. Thus, computing system 140 can be put in a registration mode where such movements can be prevented via input from a force sensor that can be used to instruct computing system 140 to not react in such a resonance or bouncing manner.

At step 518, the fiducial marker cap can be activated, such as by probe tip 210 or head 242 or head 314 engaging a switch. Activation of the fiducial marker cap can cause electronics of the fiducial marker cap to generate an electric or sensory signal. For example, an electric visual signal can be generated by a light emitting device, such as light sources 416A-416C. In other examples, an electric audio signal can be produced by the sensory feedback fiducial marker cap. In other examples, an electric signal can be sent, such as by I/O device 412 to, for example, computing system 140 or a device worn by a surgeon or operator. In an example, computing system 140 can utilize force sensor 180 (FIG. 1) to ensure or verify that robotic surgical arm 120 (FIG. 2) pushes the switch with adequate force. Furthermore, in examples, information from force sensor 180 can be used to determine if probe tip 210 has properly engaged a fiducial marker without the aid of a separate switch signal. For example, computing system 140 can be put in a cooperative mode where signals from force sensor 180 can be detected when probe tip 210 contacts the fiducial marker. Additionally, positioning of probe tip 210 can be done using a mix of cooperative and automatic modes where an operator manually moves probe tip 210 in close proximity to the fiducial marker and then computing system 140 moves probe tip 210 into actual contact with the fiducial marker. In another mixed mode operation, probe tip 210 can be manually moved into contact with fiducial markers in order to generate a three-dimensional model of the fiducial markers that can permit computing system 140 to automatically position probe tip 210 in locations to contact the fiducial markers, such as for verification with a switch or sensor described herein. In yet another mixed mode operation, probe tip 210 can be manually moved into close proximity of the fiducial markers and further movement can be controlled incrementally, such as by use of a button or remote control, until computing system 140 determines that probe tip 210 is in the proper location using switch or sensor information described herein. As an alternative to using force sensor information, or in conjunction with using force sensor information, switch information or conduction/magnetic sensing, power consumption from motors for robotic arm 120 can be used to determine if probe tip 210 contacts a fiducial marker. Such power consumption information can be correlated to force information.

At step 520, sensory feedback from the fiducial marker cap can be received by an operator of surgical system 100 either directly from the fiducial marker cap or from computing system 140. For example, the sensory feedback can comprise a visual indicator, such as light wave 424 provided by a lit up light source, from the fiducial marker cap, an audio indicator, such as sound wave 426 provided by an auditory alarm, from the fiducial marker cap, or a visual or audio indicator from human interface device 145 provided by signal 422.

At step 522, after the sensory feedback has been received by the surgeon or operator or computing system 140, a location for the fiducial marker fastener can be recorded. For example, when probe tip 210 engages the fiducial marker cap, the orientation of robotic surgical arm 120 can be recorded in memory of computing system 140. The orientation of robotic surgical arm 120 can be determined using, for example, tracking element 170 and the known geometry of pointer probe 200 or the orientation of segments of robotic surgical arm 120 relative to axes 216A-216D and the known geometry of pointer probe 200. The location can be manually recorded by a surgeon or operator using computing system 140, or computing system 140 can automatically record the location when signal 422 is generated.

At step 524, engagement of probe tip 210 with the fiducial marker cap can be confirmed. Confirmation can comprise withdrawing probe tip 210 from the fiducial marker cap and reengaging probe tip 210 with the fiducial marker cap. As such, method 500 can return to step 516 or another step of method 500 to receive additional sensory feedback and record another location for the fiducial marker fastener location.

In examples, a switch for the fiducial marker cap can remain activated such that the sensory feedback remains active. When the probe tip reactivates the switch, the sensory feedback can change. For example, the sensory feedback can change from a first color to a second color so a surgeon or operator can visually track the sequence of confirmation. In various embodiments, the confirmation can be repeated twice such that three data points can be collected for each fiducial marker fastener. In other examples, the switch for the fiducial marker cap can deactivate when the pointer probe disengages. Thus, the same sensory feedback can be provided for each time the pointer probe engages the fiducial marker cap and a surgeon or operator can manually keep track of the number of data points collected, such as with the aid of computing system 140.

At step 526, the fiducial marker cap can be deactivated, such as by withdrawing the pointer probe from the fiducial marker cap. Additionally, the fiducial marker cap can be reengaged by probe tip 210 to deactivate the fiducial marker cap. In other examples, the fiducial marker cap can be left activated. After the location for a fiducial marker is successfully recorded, robotic surgical arm 120 can be manipulated to repeat the process to record the location for another fiducial marker at a different location on the patient. As such, the process or method can return to step 510 or another step to repeat all of some of method 500.

Figure 15:
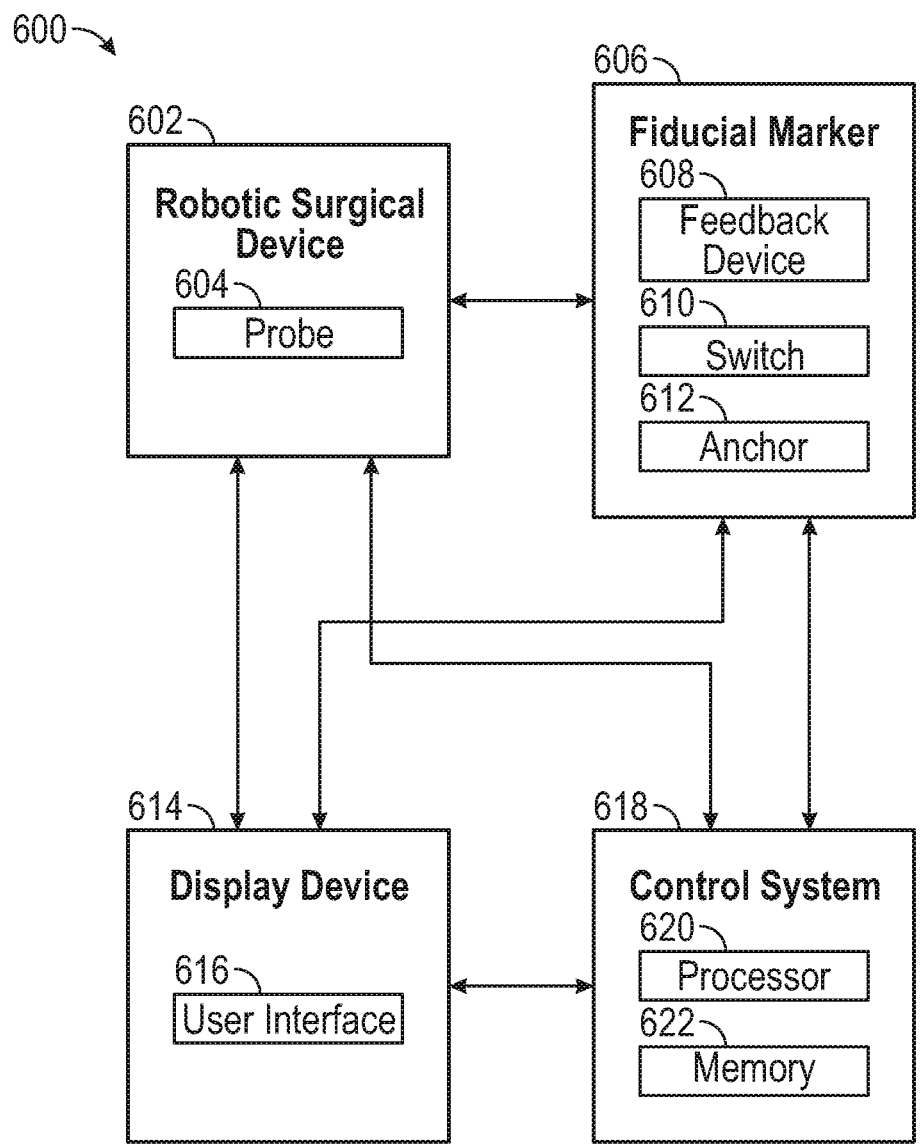
FIG. 15 is a schematic illustration of a robotic surgical system incorporating fiducial markers of the present application.

FIG. 15 illustrates system 600 for performing techniques described herein, in accordance with some embodiments. System 600 can include robotic surgical device 602 coupled to probe 604, which may interact with fiducial marker 606. Fiducial marker 606 can include sensory component 608, switch component 610 and anchor component 612. System 600 can include display device 614, which can be used to display user interface 616. System 600 can include control system 618 (e.g., a robotic controller), including processor 620 and memory 622. In an example, display device 614 can be coupled to one or more of robotic surgical device 602, probe device 606, or control system 618.

Figure 16:
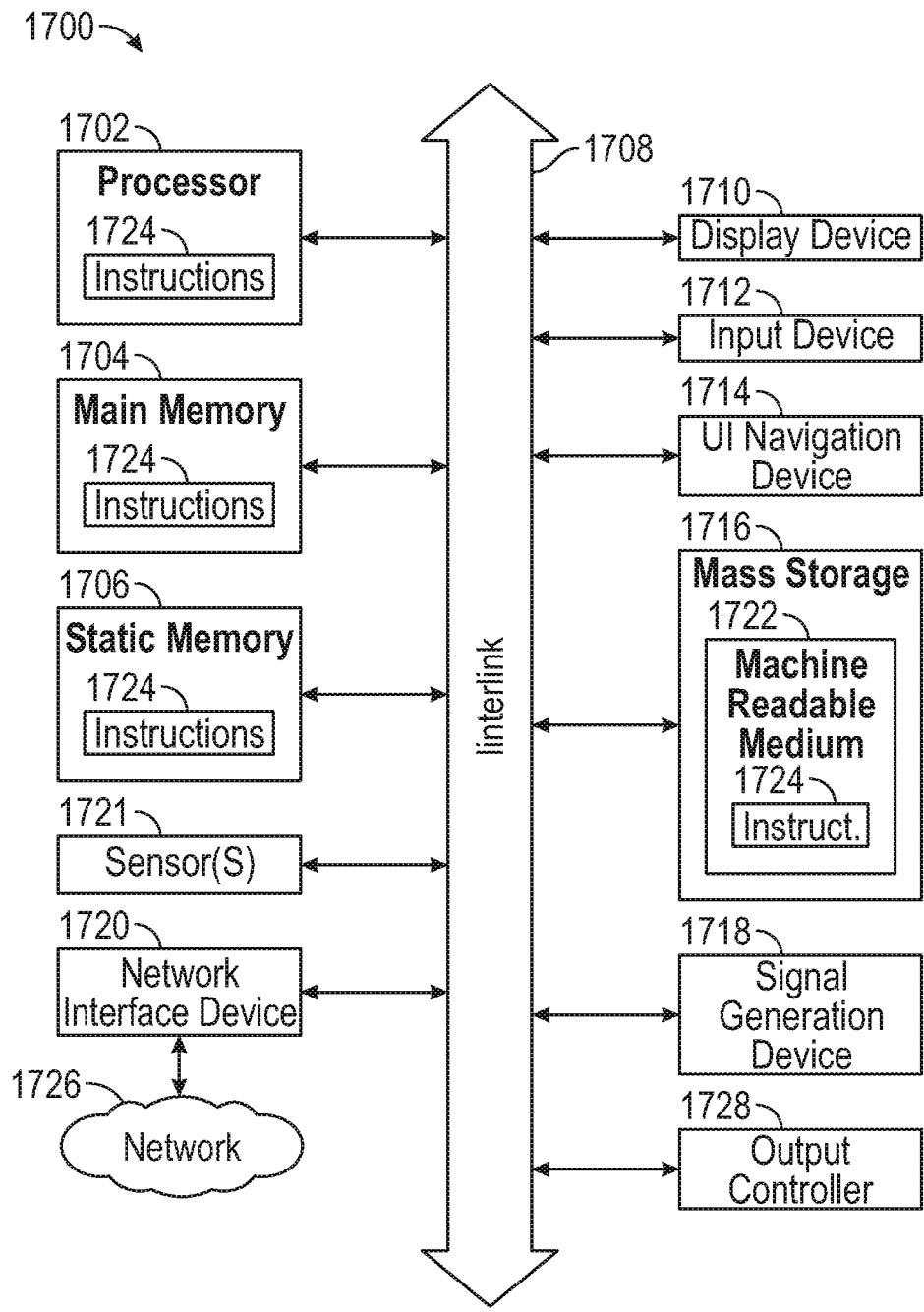
FIG. 16 is a schematic illustration of a block diagram of an example machine upon which any one or more of the techniques discussed herein may perform and with which any of the devices discussed herein may be used in accordance with some embodiments.

FIG. 16 illustrates a block diagram of an example machine 1700 upon which any one or more of the techniques discussed herein may perform in accordance with some embodiments. In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-FI®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MEMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing registration processes of fiducial markers with robotic surgical systems, such as by improving the accuracy of the registration process. In particular, the systems, devices and methods described herein facilitate more precise engagement between a pointer probe tip and a fiducial marker and better recognition of proper engagement between a pointer probe tip and the fiducial marker by an operator or surgeon. Such

VARIOUS NOTES & EXAMPLES benefits can reduce error in the registration process, which can correlate to reduced error in performing a medical procedure on a patient.

Example 1 can include or use subject matter such as a fiducial marker that can comprise a fastener comprising a threaded shaft extending along an axis and a head connected to the threaded shaft, and a feedback component attached to the fastener, wherein the feedback component is configured to provide a registration signal when engaged by a probe.

Example 2 can include, or can optionally be combined with the subject matter of Example 1, to optionally include a feedback component comprising a housing attached to the head, the housing comprising an access port disposed in a first end of the housing, a switch disposed in the housing proximate the access port, and a light source electronically coupled to the switch, wherein the light source is configured to emit light when the switch is activated through the access port.

Example 3 can include, or can optionally be combined with the subject matter of one or any combination of Examples 1 or 2 to optionally include a light source comprising a light-emitting diode and a housing that can be translucent or transparent.

Example 4 can include, or can optionally be combined with the subject matter of one or any combination of Examples 1 through 3 to optionally include a housing that can include a socket disposed in a second end of the housing opposite the first end for receiving the head of the fastener.

Example 5 can include, or can optionally be combined with the subject matter of one or any combination of Examples 1 through 4 to optionally include a housing that can comprise a body for receiving the switch and the light source and a plurality of fingers extending from the body to form the socket and receive the head of the fastener.

Example 6 can include, or can optionally be combined with the subject matter of one or any combination of Examples 1 through 5 to optionally include a fastener that can include a circumferential channel and each of the plurality of fingers of the housing that can include a radially inwardly extending tab configured to engage the channel in the fastener.

Example 7 can include, or can optionally be combined with the subject matter of one or any combination of Examples 1 through 6 to optionally include a housing that can comprise a prong for engaging a socket in an end of the head of the fastener.

Example 8 can include, or can optionally be combined with the subject matter of one or any combination of Examples 1 through 7 to optionally include a power source coupled to the switch within the housing.

Example 9 can include, or can optionally be combined with the subject matter of one or any combination of Examples 1 through 8 to optionally include a light source that can be configured to emit light of a plurality of different colors.

Example 10 can include, or can optionally be combined with the subject matter of one or any combination of Examples 1 through 9 to optionally include a light source that can be configured to emit a single color after consecutive activations of the switch, wherein the single color is different for each consecutive activation.

Example 11 can include, or can optionally be combined with the subject matter of one or any combination of Examples 1 through 10 to optionally include an output device that can be configured to electronically communicate a status of the switch to a computing system.

Example 12 can include, or can optionally be combined with the subject matter of one or any combination of Examples 1 through 11 to optionally include a feedback component that is integral with the head of the fastener, the feedback component being selected from the group consisting of a conducting material, a magnetic material and a radio frequency identification tag.

Example 13 can include or use subject matter such as a cap for use in registering a fiducial marker with a robotic surgical system that can comprise a housing, a socket disposed in a first end of the housing configured to couple to a component for the robotic surgical system, an access port disposed in a second end of the housing opposite the socket, a switch disposed in the housing proximate the access port and a sensory indicator device coupled to the switch, wherein the sensory indicator device is configured to produce an electronic signal when the switch is activated through the access port to provide sensory confirmation that the fiducial marker has been engaged.

Example 14 can include, or can optionally be combined with the subject matter of Example 13, to optionally include a component for the robotic surgical system that can comprise either a head for a fiducial marker fastener or a tip of a pointer probe and a socket that can comprise a plurality of fingers configured to flex around the component.

Example 15 can include, or can optionally be combined with the subject matter of one or any combination of Examples 13 or 14 to optionally include a sensory indicator device that can comprise a light source and a housing that can be fabricated from a translucent or transparent material.

Example 16 can include, or can optionally be combined with the subject matter of one or any combination of Examples 13 through 15 to optionally include an electronic indicator that can comprise an electronic communication signal.

Example 17 can include, or can optionally be combined with the subject matter of one or any combination of Examples 13 through 16 to optionally include a power source located within the housing to power the sensory indicator device when the switch is activated.

Example 18 can include or use subject matter such as a method of registering a fiducial marker that can comprise attaching a signal-producing cap to a component of the robotic surgical system, manipulating a pointer probe to align the signal-producing cap and the fiducial marker fastener with the pointer probe, engaging a probe tip of the pointer probe, a switch attached to the signal-producing cap and the fiducial marker fastener to activate a sensory feedback indicator, receiving the sensory feedback indicator from the signal-producing cap and recording a location for the fiducial marker fastener in a coordinate system for the robotic surgical system.

Example 19 can include, or can optionally be combined with the subject matter of Example 18, to optionally include a component of the robotic surgical system that can comprise a head of the fiducial marker fastener.

Example 20 can include, or can optionally be combined with the subject matter of one or any combination of Examples 18 or 19 to optionally include engaging the probe tip of the pointer probe with the switch attached to the signal-producing cap and the fiducial marker to activate the sensory feedback indicator that can comprise inserting the probe tip through an access port in the signal-producing cap.

Example 21 can include, or can optionally be combined with the subject matter of one or any combination of Examples 18 through 20 to optionally include engaging the probe tip of the pointer probe with the switch attached to the signal-producing cap to activate the sensory feedback indicator that can comprise activating a light source of the signal-producing cap to confirm engagement of the probe tip with the fiducial marker fastener.

Example 22 can include, or can optionally be combined with the subject matter of one or any combination of Examples 18 through 21 to optionally include manipulating the pointer probe to align the signal-producing cap and the fiducial marker fastener with the pointer probe that can comprise manipulating a robotic surgical arm connected to the pointer probe.

Example 23 can include, or can optionally be combined with the subject matter of one or any combination of Examples 18 through 22 to optionally include imaging a fiducial marker fastener to produce an image, and mapping the image to the coordinate system Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A fiducial marker comprising:
   a fastener comprising:
      a threaded shaft extending along an axis; and
      a head connected to the threaded shaft;
   a feedback component attached to the fastener; and
   a switch in communication with the feedback component,
   wherein the feedback component is configured to provide an electronic registration signal when the switch is engaged by a probe.

2. The fiducial marker of claim 1, wherein the feedback component comprises:
   a housing attached to the head, the housing comprising an access port disposed in a first end of the housing; and
   a light source electronically coupled to the switch;
   wherein the switch is disposed in the housing aligned with the access port so as to be engageable by the probe;
   wherein the light source is configured to emit light when the switch is activated through the access port; and
   wherein the switch is displaceable by the probe from a first position wherein the light source is deactivated and a second position where the light source is activated.

3. The fiducial marker of claim 2, wherein:
   the light source comprises a light-emitting diode; and
   the housing is translucent or transparent.

4. The fiducial marker of claim 2, wherein the housing includes a socket disposed in a second end of the housing opposite the first end for receiving the head of the fastener, wherein the socket is configured to attach to the head of the fastener in a releasable manner.

5. The fiducial marker of claim 4, wherein the housing comprises:
   a body for receiving the switch and the light source; and
   a plurality of fingers extending from the body to form the socket and receive the head of the fastener.

6. The fiducial marker of claim 5, wherein:
the fastener includes a circumferential channel; and
each of the plurality of fingers of the housing includes a radially inwardly extending tab configured to engage the circumferential channel in the fastener.

7. The fiducial marker of claim 2, wherein the housing comprises a prong for engaging a socket in an end of the head of the fastener.

8. The fiducial marker of claim 2, further comprising a power source coupled to the switch within the housing.

9. The fiducial marker of claim 2, wherein the light source is configured to emit light of a plurality of different colors.

10. The fiducial marker of claim 9, wherein the light source is configured to emit a single color after consecutive activations of the switch, wherein the single color is different for each consecutive activation.

11. The fiducial marker of claim 2, further comprising an output device configured to electronically communicate a status of the switch to a computing system.

12. The fiducial marker of claim 2, wherein the registration signal comprises an electronic registration signal and the feedback component is configured to generate the electronic registration signal when the switch is engaged by a probe.

13. The fiducial marker of claim 12, wherein:
the switch is disposed in the housing aligned with the access port so as to be engageable by the probe; and
the switch is displaceable by the probe from a first position wherein the light source is deactivated and a second position where the light source is activated.

14. The fiducial marker of claim 2, further comprising a button disposed in the access port and coupled to the switch.

15. The fiducial marker of claim 14, wherein:
the housing defines an internal compartment;
the access port extends from an exterior of the housing to the internal compartment;
the button is sealed against the access port; and
the switch is within the internal compartment.

16. The fiducial marker of claim 1, wherein the feedback component is integral with the head of the fastener, the feedback component being selected from the group consisting of a conducting material, a magnetic material and a radio frequency identification tag.

17. The fiducial marker of claim 1, wherein the registration signal comprises an electronic communication signal.

18. A fiducial marker with a robotic surgical system, the fiducial marker comprising:
a cap comprising:
a housing defining an internal compartment;
a socket disposed in a first end of the housing;
an access port disposed in a second end of the housing opposite the socket to connect to the internal compartment;
an on-off switch disposed in the internal compartment of the housing proximate the access port; and
a sensory indicator device coupled to the on-off switch;
wherein the sensory indicator device is configured to produce an electronic signal when the on-off switch is mechanically activated through the access port to provide sensory confirmation that the fiducial marker has been engaged; and
a fastener connectable to the cap.

19. The fiducial marker of claim 18, wherein:
the socket comprises a plurality of fingers configured to flex around the component.

20. The fiducial marker of claim 18, wherein:
the sensory indicator device comprises a light source; and
the housing is fabricated from a translucent or transparent material.

21. The fiducial marker of claim 18, wherein the electronic signal comprises an electronic communication signal or a registration signal.

22. The fiducial marker of claim 18, further comprising a power source located within the housing to power the sensory indicator device when the on-off switch is activated.

23. A method of registering a fiducial marker, the method comprising:
attaching a signal-producing cap to a fiducial marker fastener of a robotic surgical system, the fiducial marker fastener comprising a threaded shaft and a head;
manipulating a pointer probe to align the signal-producing cap and the fiducial marker fastener with the pointer probe;
engaging a probe tip of the pointer probe, a switch attached to the signal-producing cap and the fiducial marker fastener to activate a sensory feedback indicator generated by a feedback component attached to the signal-producing cap;
receiving the sensory feedback indicator from the signal-producing cap; and
recording a location for the fiducial marker fastener in a coordinate system for the robotic surgical system;
wherein the sensory feedback indicator comprises an electronic registration signal.

* * * * *